United States Patent
Asanuma

(12) 
(10) Patent No.: US 10,036,908 B2
(45) Date of Patent: Jul. 31, 2018

(54) MEDICAL MONITOR, ELECTRONIC APPARATUS, AND VIDEO DISPLAY UNIT

(71) Applicant: TOSHIBA VISUAL SOLUTIONS CORPORATION, Misawa (JP)

(72) Inventor: Reiya Asanuma, Tokyo (JP)

(73) Assignee: TOSHIBA VISUAL SOLUTIONS CORPORATION, Misawa-Shi (JP)

( * ) Notice: Subject to any disclaimer, the term of this patent is extended or adjusted under 35 U.S.C. 154(b) by 228 days.

(21) Appl. No.: 14/927,345

(22) Filed: Oct. 29, 2015

(65) Prior Publication Data

US 2016/0291387 A1    Oct. 6, 2016

(30) Foreign Application Priority Data

Apr. 3, 2015 (JP) ................. 2015-077091

(51) Int. Cl.
  *G02F 1/133* (2006.01)
  *G02F 1/1333* (2006.01)
  *A61B 90/00* (2016.01)

(52) U.S. Cl.
  CPC ........ *G02F 1/133308* (2013.01); *A61B 90/37* (2016.02)

(58) Field of Classification Search
  CPC ...................................................... G02F 1/33
  USPC .......................................................... 348/836
  See application file for complete search history.

(56) References Cited

FOREIGN PATENT DOCUMENTS

| EP | 1291668 A2 | * | 3/2003 | .............. G01S 11/12 |
|---|---|---|---|---|
| JP | 2005-070661 | | 3/2005 | |
| JP | 2005-070662 | | 3/2005 | |
| JP | 2005070661 A | * | 3/2005 | |
| JP | 2005070662 A | * | 3/2005 | |
| JP | 2006246307 A | * | 9/2006 | |

* cited by examiner

*Primary Examiner* — Chikaodili E Anyikire
*Assistant Examiner* — Shanika Brumfield
(74) *Attorney, Agent, or Firm* — Rutan & Tucker, LLP

(57) ABSTRACT

According to one embodiment, a medical monitor includes a housing, a display panel, a phototransmissive front panel and a support portion. The phototransmissive front panel includes a first surface, a second surface and a locking surface. The first surface faces the display screen. The second surface is located on an opposite side to the first surface and is exposed to an outside. The locking surface is provided along at least one side of the second surface and is located inward of the second surface in the housing in a thickness direction of the display panel. The support portion is provided in the housing. The support portion faces the locking surface from the outside in the thickness direction of the display panel.

12 Claims, 19 Drawing Sheets

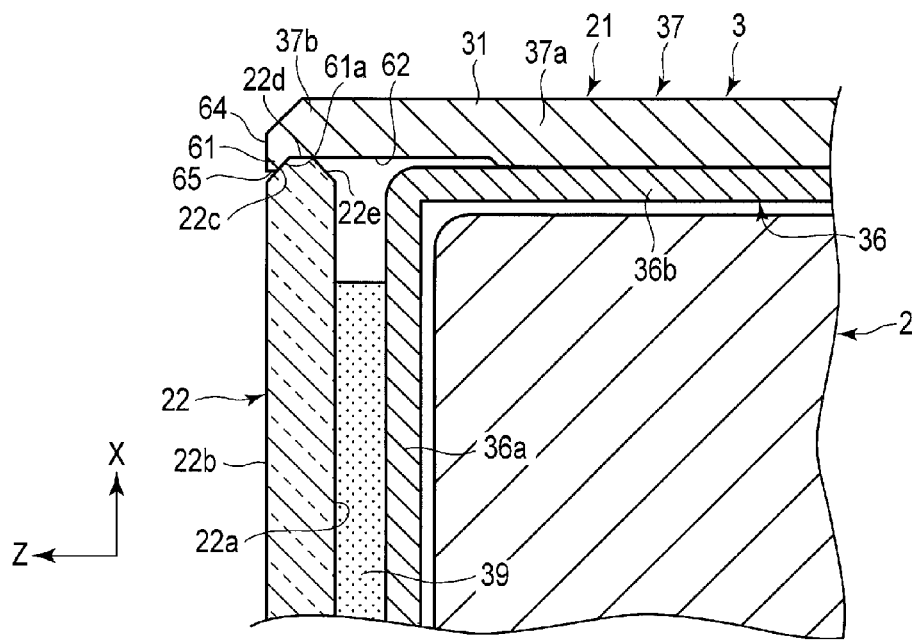
F I G. 4
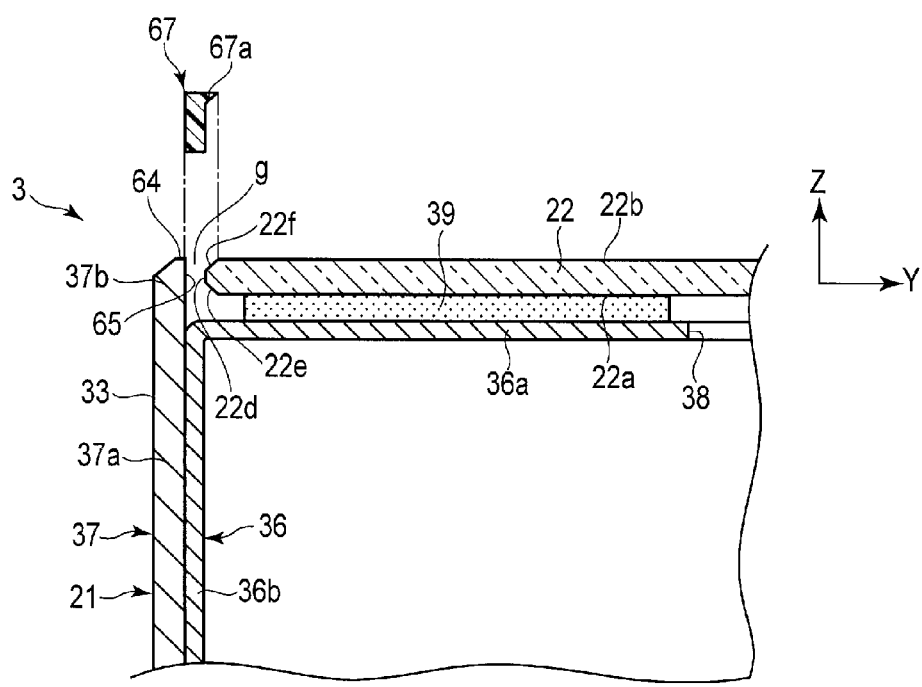
F I G. 5

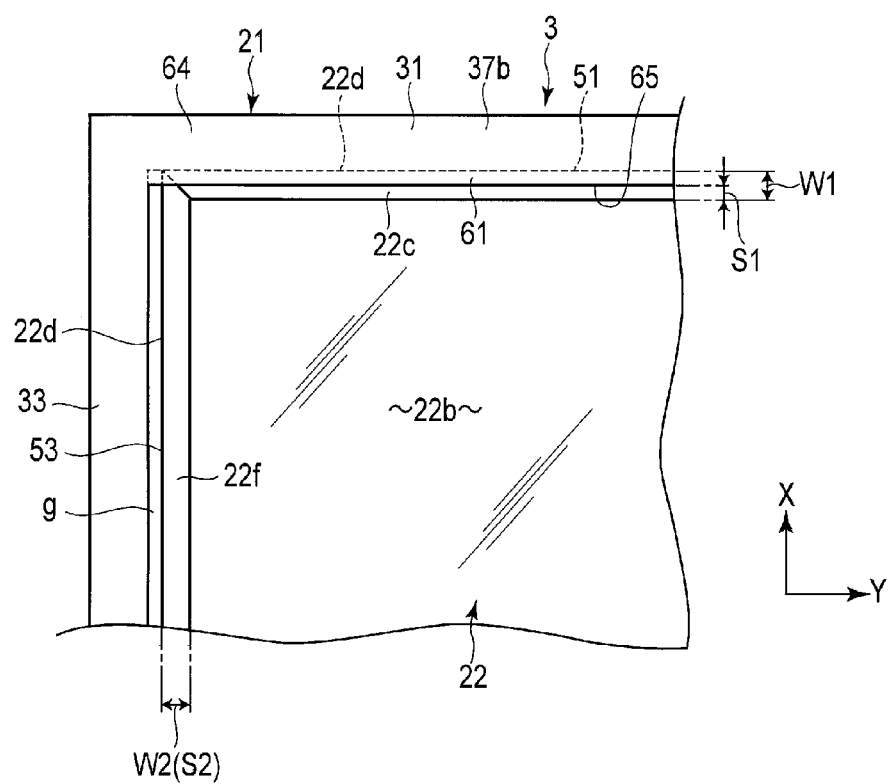
F I G. 6

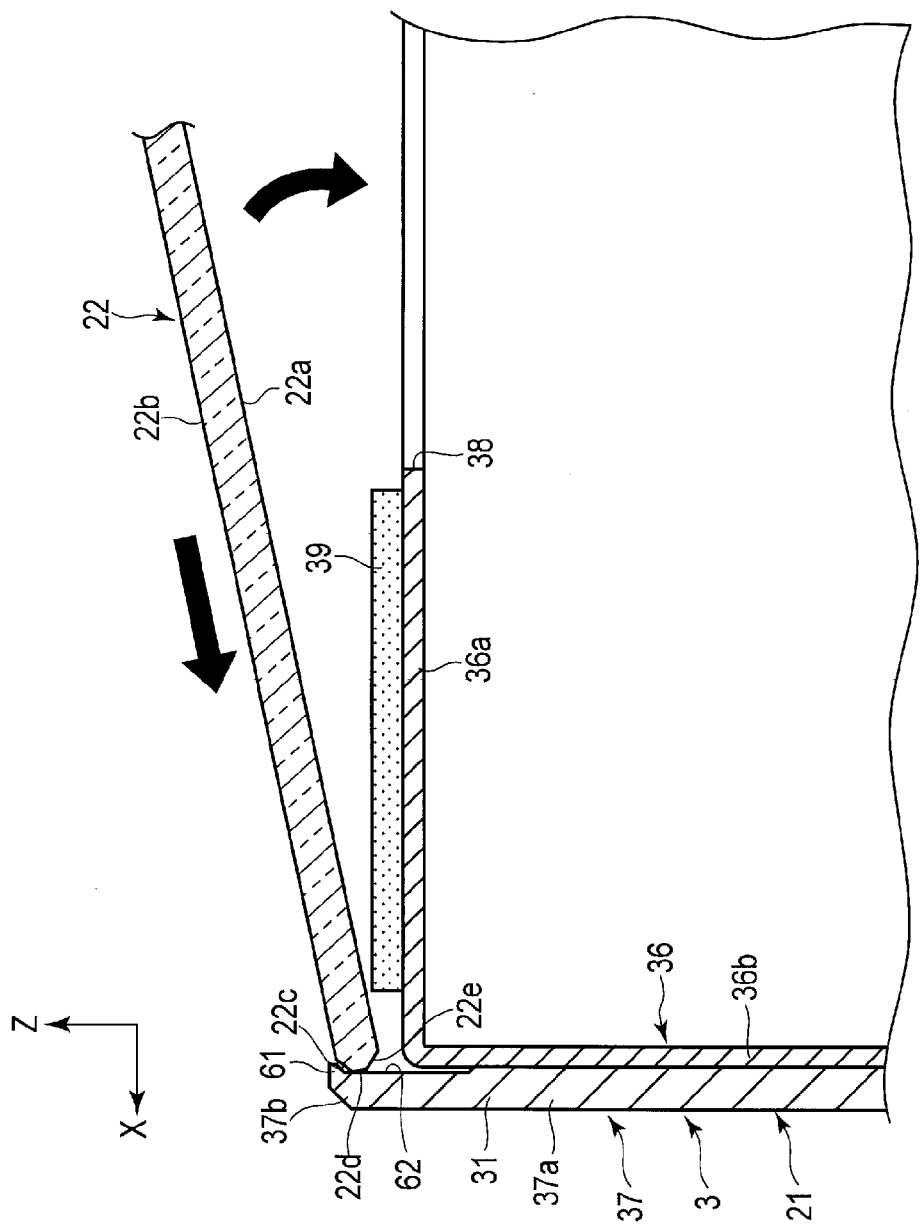
F I G. 7

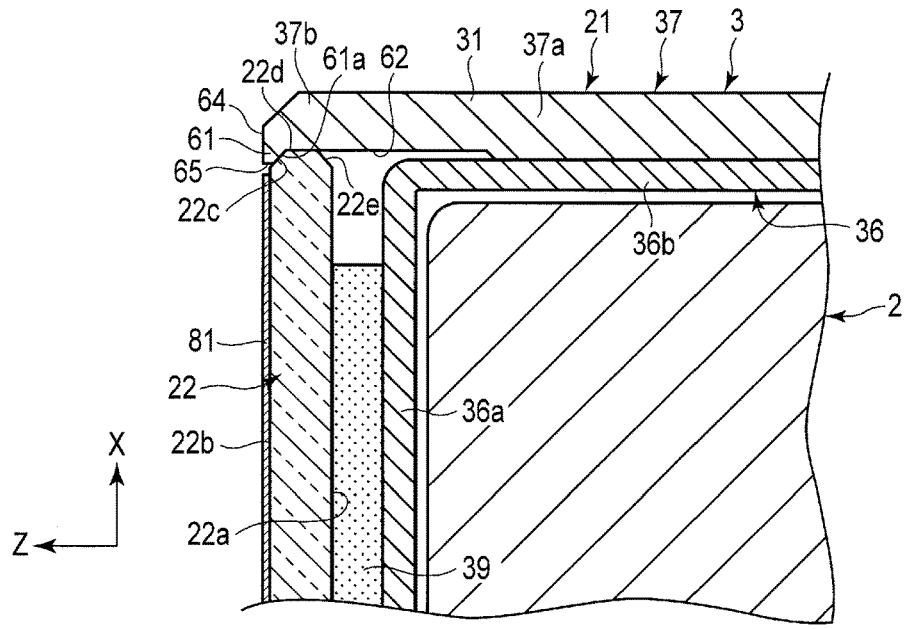
F I G. 11
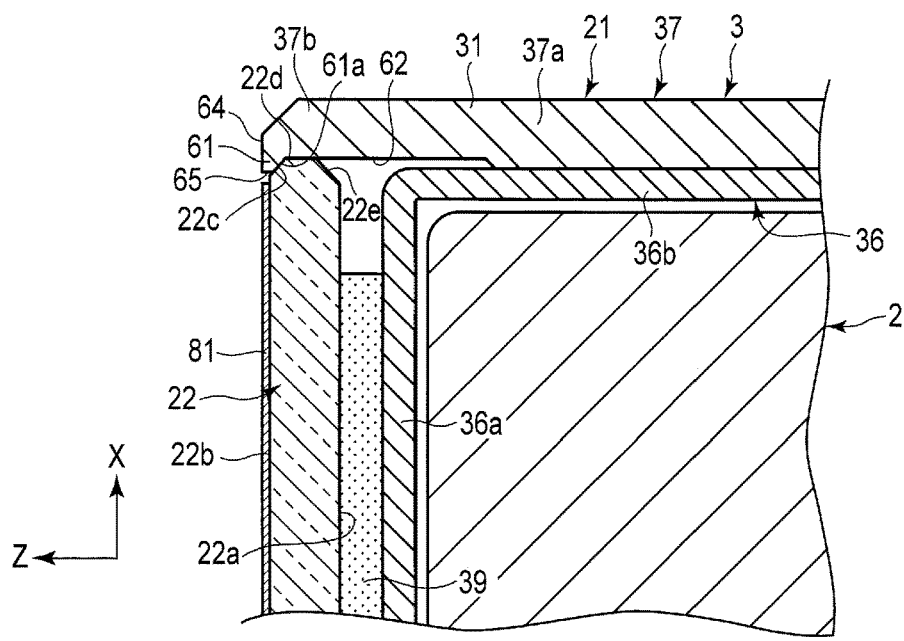
F I G. 12

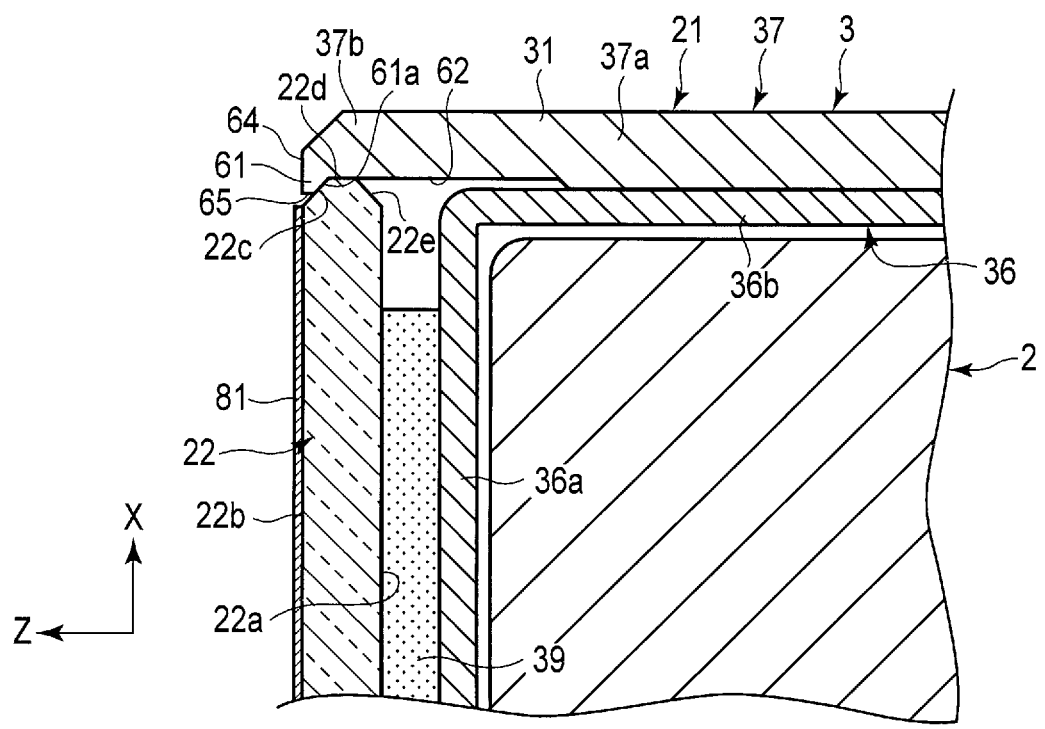
F I G. 13

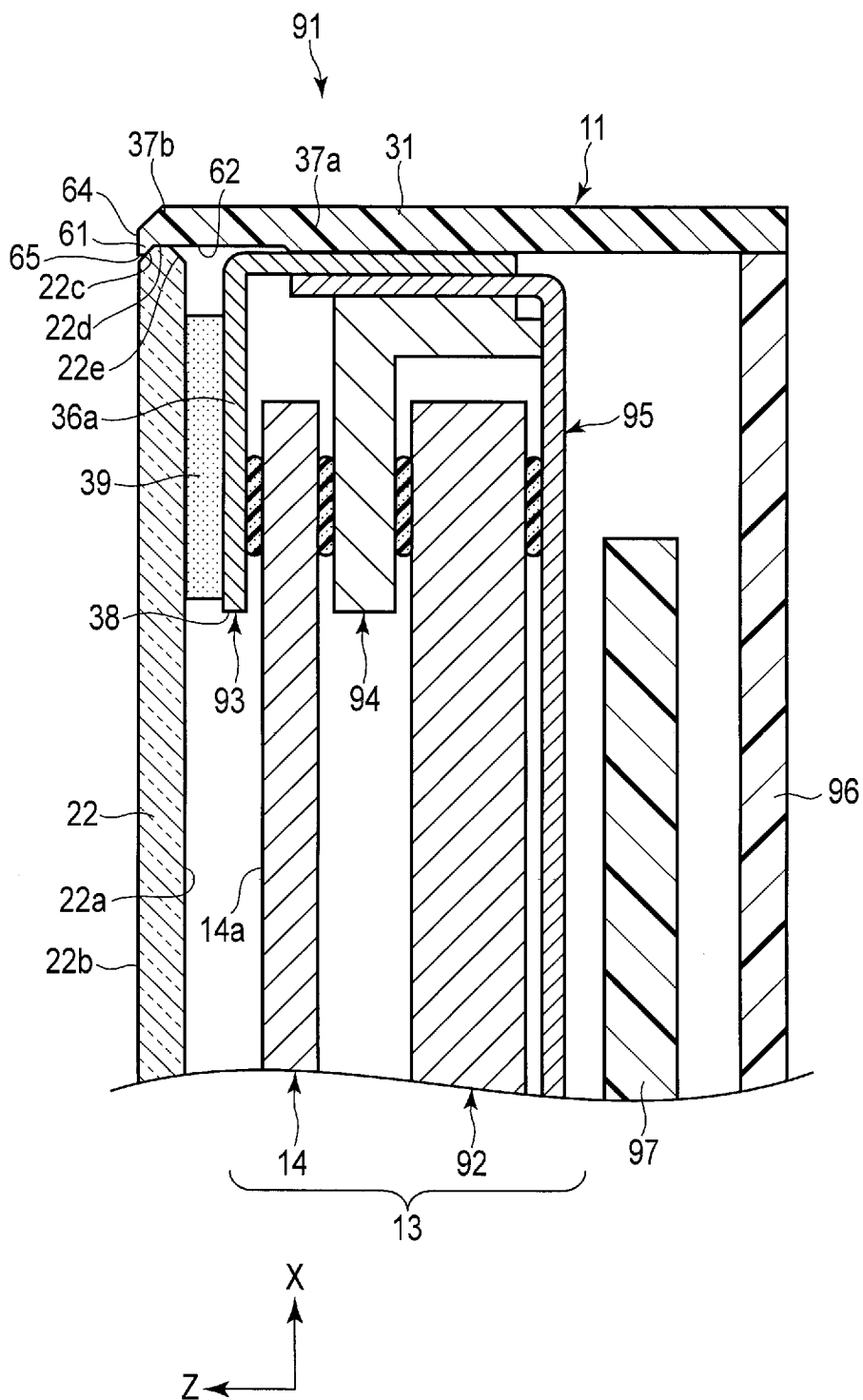
F I G. 15

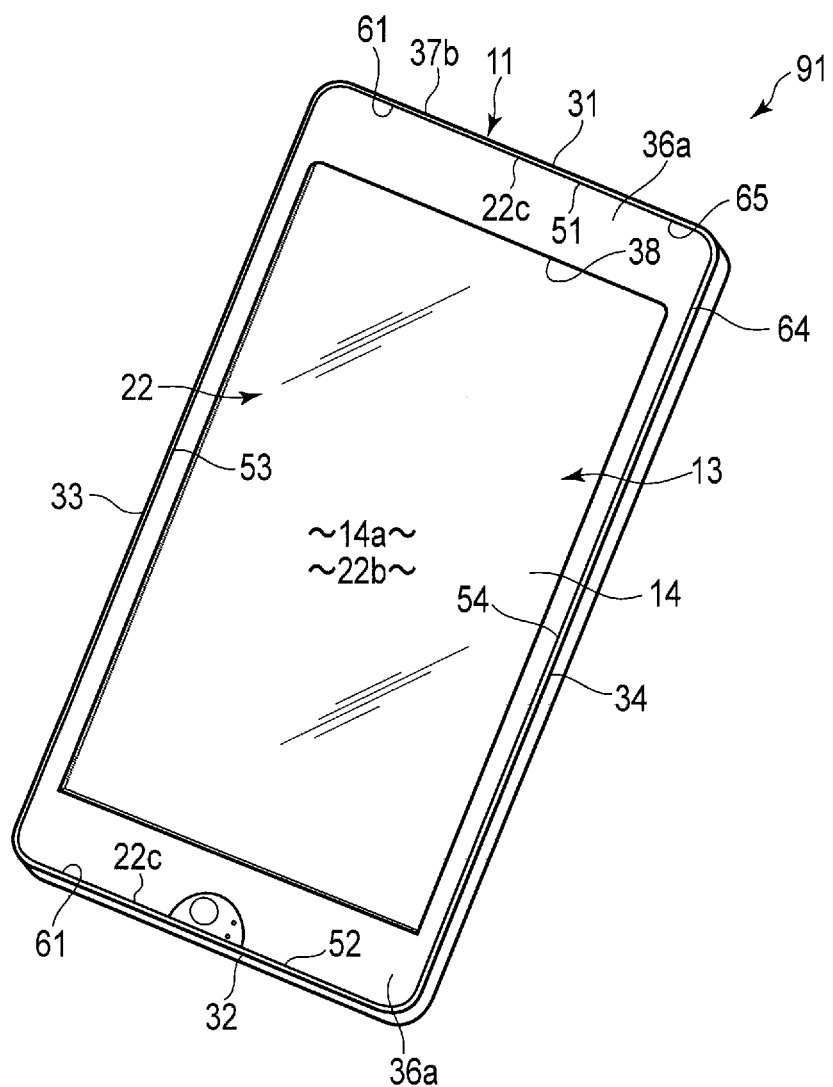
F I G. 17

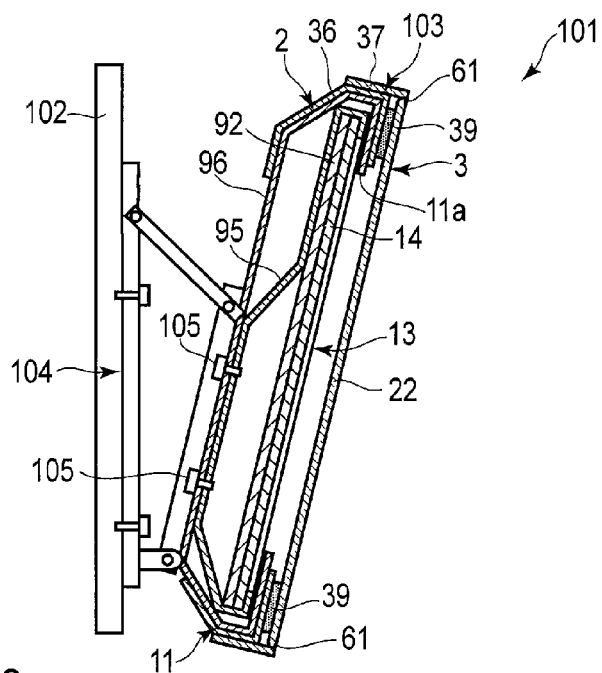
F I G. 18
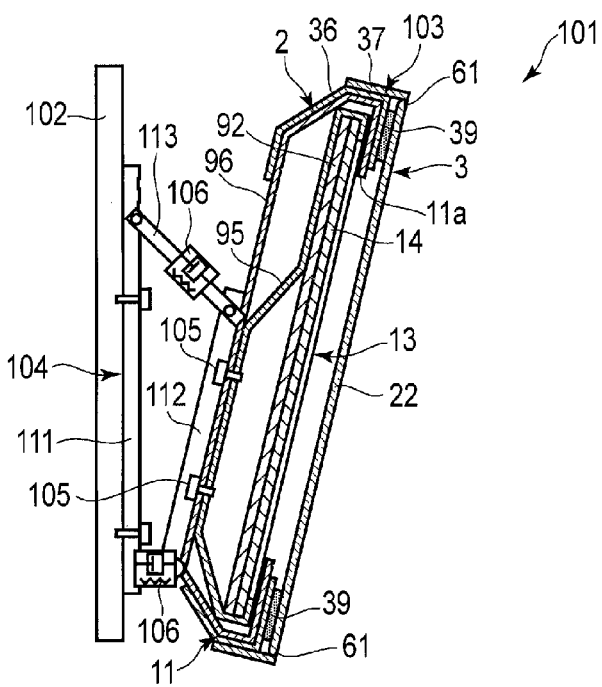
F I G. 19

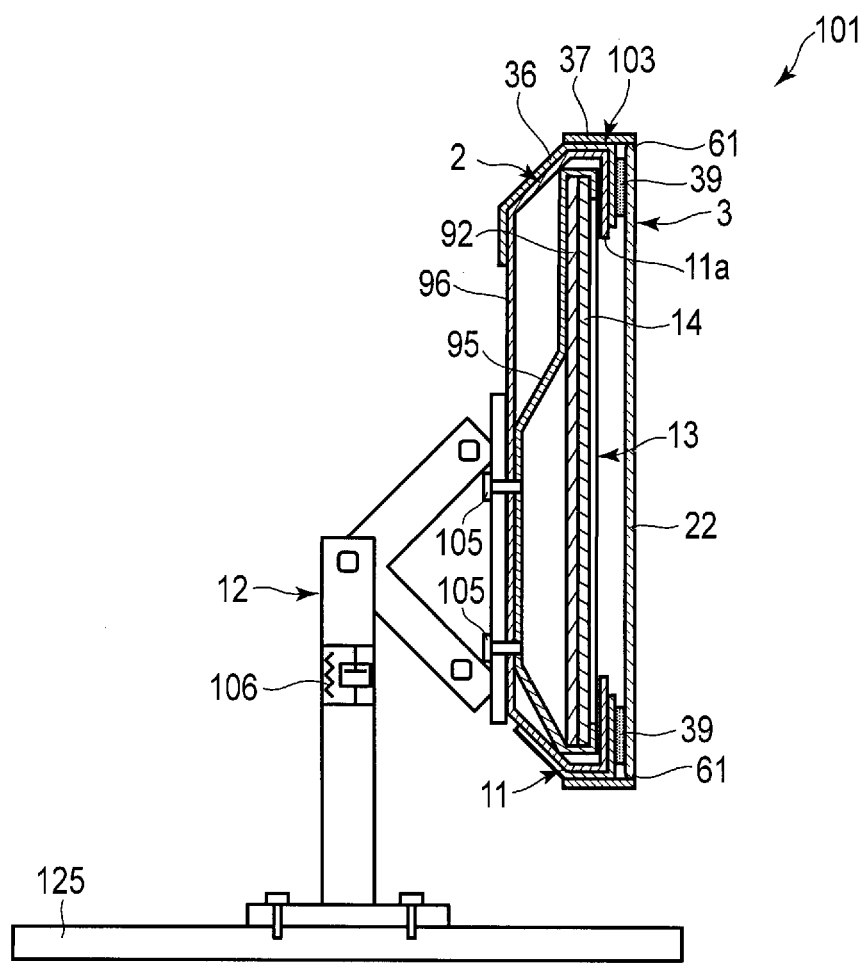
F I G. 21

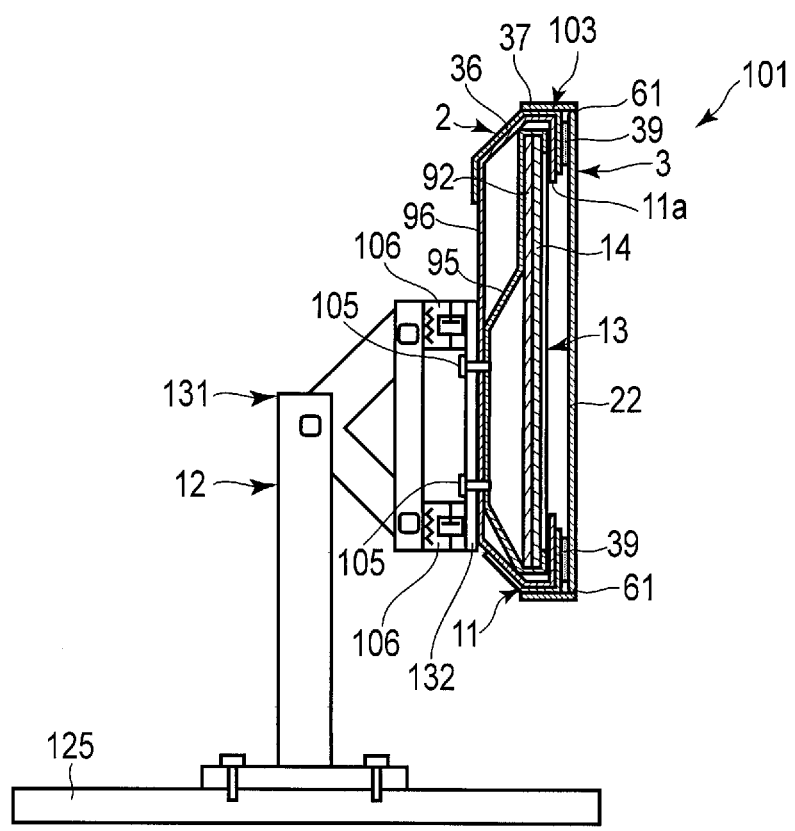
F I G. 22 ional Patent Application No. 2015-077091,
MEDICAL MONITOR, ELECTRONIC APPARATUS, AND VIDEO DISPLAY UNIT

CROSS-REFERENCE TO RELATED APPLICATIONS

This application is based upon and claims the benefit of priority from Japanese Patent Application No. 2015-077091, filed Apr. 3, 2015, the entire contents of which are incorporated herein by reference.

FIELD

Embodiments described herein relate generally to a medical monitor, an electronic apparatus, and a video display unit.

BACKGROUND

Electronic apparatuses with a phototransmissive front panel forward of a display panel have been provided.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 4 is a cross-sectional view illustrating a region enclosed in line F4 shown in FIG. 3 enlargingly.

FIG. 5 is a cross-sectional view taken along line F5-F5 of the protective cover shown in FIG. 3.

FIG. 6 is a front view illustrating a region enclosed in line F6 shown in FIG. 2 enlargingly.

FIG. 7 is a cross-sectional view illustrating an example of an assembling method of the protective cover shown in FIG. 1.

FIG. 11 is a cross-sectional view illustrating the protective cover according to a third modification of the first embodiment.

FIG. 12 is a cross-sectional view illustrating a further modification of the protective cover shown in FIG. 11.

FIG. 13 is a cross-sectional view illustrating a further modification of the protective cover shown in FIG. 11.

FIG. 15 is a cross-sectional view taken along line F15-F15 of the television receiver shown in FIG. 14.

FIG. 17 is a perspective view illustrating a smartphone according to a fourth embodiment.

FIG. 18 is a cross-sectional view illustrating a video display unit according to a fifth embodiment.

FIG. 19 is a cross-sectional view illustrating the video display unit according to a first modification of the fifth embodiment.

FIG. 21 is a cross-sectional view illustrating the video display unit according to a third modification of the fifth embodiment.

FIG. 22 is a cross-sectional view illustrating the video display unit according to a fourth modification of the fifth embodiment.

DETAILED DESCRIPTION

Various embodiments will be described hereinafter with reference to the accompanying drawings.

In general, according to one embodiment, a medical monitor is configured to display a medical stereoscopic image. The medical monitor includes a housing, a display panel, a phototransmissive front panel and a support portion.

The display panel is accommodated in the housing. The display panel includes a display screen.

The phototransmissive front panel includes a first surface, a second surface and a locking surface. The first surface faces the display screen. The second surface is located on an opposite side to the first surface and is exposed to an outside. The locking surface is provided along at least one side of the second surface and is located inward of the second surface in the housing in a thickness direction of the display panel.

The support portion is provided in the housing. The support portion faces the locking surface from the outside in the thickness direction of the display panel.

In this specification, some elements are each expressed by two or more terms. These terms are merely examples and the elements may be expressed by other terms. The other elements, which are not expressed by two or more terms, may also be expressed by other terms.

First Embodiment

Figure 1:
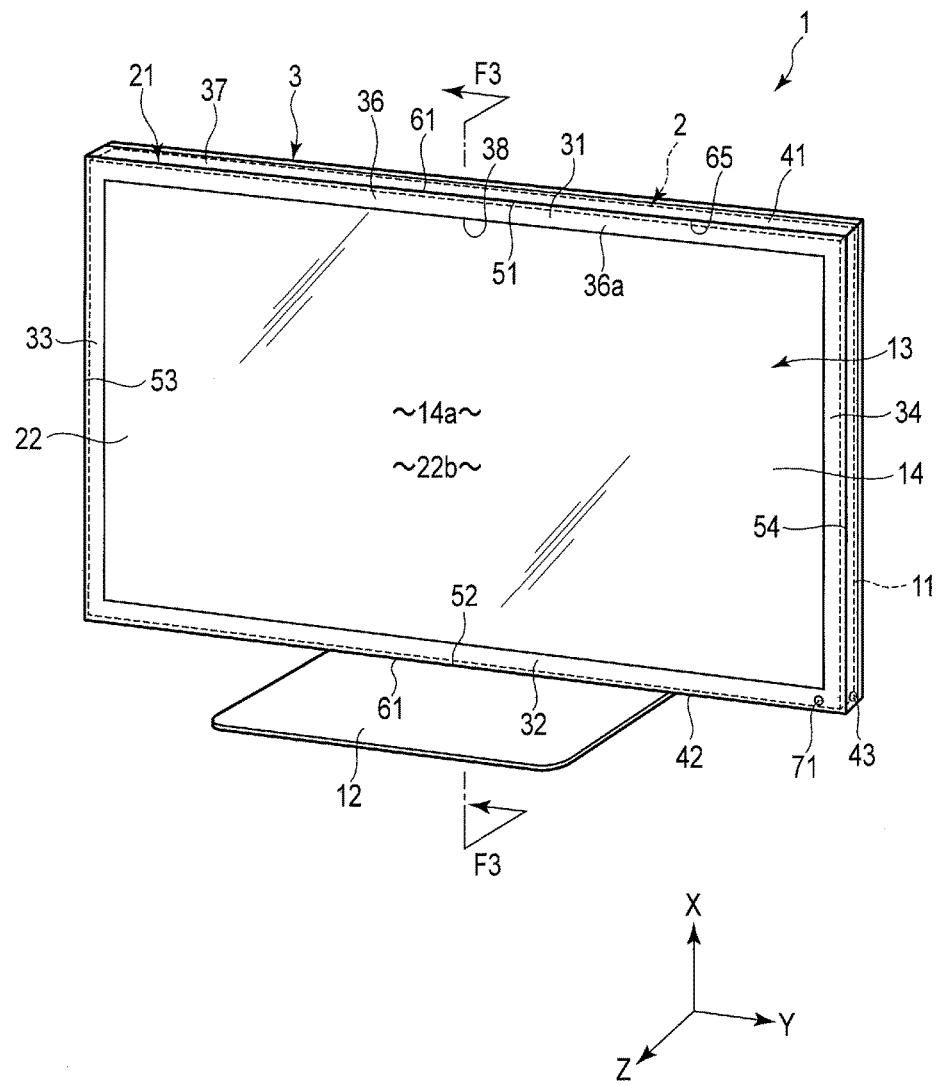
FIG. 1 is a perspective view illustrating a video display unit according to a first embodiment.
Figure 2:
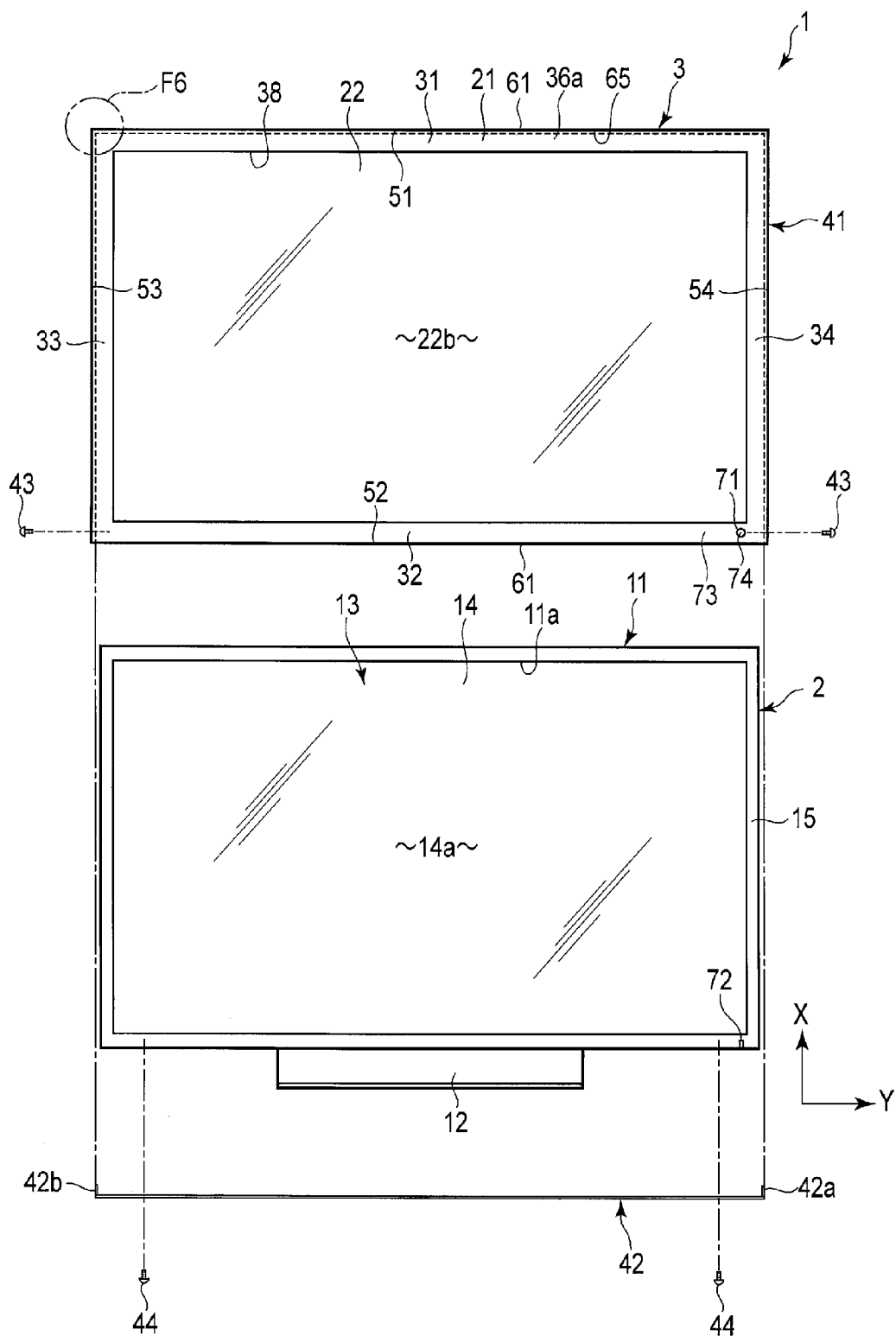
FIG. 2 is a front view illustrating a protective cover shown in FIG. 1.

FIG. 1 shows a video display unit 1 according to a first embodiment. As shown in FIG. 2, the video display unit 1 includes a video display apparatus 2 and a protective cover 3 mounted on the video display apparatus 2. The video display apparatus 2 is, for example, a monitor. It should be noted that the present embodiment is applicable not only to the above-described video display apparatus, but is widely applicable to various electronic apparatuses such as digital signage, tablet terminals (multifunctional portable terminals), smartphones, and television receivers.

As shown in FIG. 2, the video display apparatus 2 comprises a housing 11 and a stand 12. The stand 12 is mounted on, for example, a back surface of the housing 11, and holds the housing 11 in a vertical attitude. It should be noted that the video display apparatus 2 may be of a wall-hung type not comprising the stand 12.

The housing 11 accommodates a display 13. The display 13 is, for example, a liquid crystal display, and includes a display panel 14 (liquid crystal panel) and a backlight unit located behind the display panel 14. It should be noted that the display 13 is not limited to a liquid crystal display, but may also be, for example, a plasma display and an organic electroluminescent (EL) display. The display panel 14 comprises a display screen 14a on which images (including still images and moving images) can be displayed.

The housing 11 is formed in the shape of a flat rectangular box. The housing 11 comprises a front bezel 15 and a unit cover (back cover). In the present embodiment, the housing 11 is formed by combining the front bezel 15 and the unit cover. The front bezel 15 forms a front surface of the housing 11, and comprises an opening 11a through which the display screen 14a of the display 13 is exposed to the outside. The unit cover covers the back of the display 13.

Next, the protective cover 3 will be described.

As shown in FIG. 1 and FIG. 2, the protective cover 3 is formed in the shape of a box one size larger than the housing 11 of the video display apparatus 2, and is mounted on the housing 11 from the outside. The protective cover 3 comprises a frame 21 and a front panel 22 mounted on a front surface of the frame 21.

The frame 21 comprises a first side 31, a second side 32, a third side 33, and a fourth side 34. The first side 31 is located at an upper end of the frame 21, and extends in a substantially horizontal direction. The second side 32 is located at a lower end of the frame 21, and extends substantially parallel to the first side 31. The third side 33 is located at a left end of the frame 21. The fourth side 34 is located at a right end of the frame 21. The third side 33 and the fourth side 34 extend in a substantially vertical direction, and connect the first side 31 and the second side 32. The frame 21 is formed by these first to fourth sides 31, 32, 33 and 34.

First to third directions X, Y and Z will be herein defined. Each of the first direction X and the second direction Y is a direction along the display screen 14a. The first direction X is a direction from the second side 32 to the first side 31. The second direction Y is a direction substantially orthogonal to the first direction X, and is a direction from the third side 33 to the fourth side 34. The third direction Z is a direction substantially orthogonal to the first direction X and the second direction Y, is a thickness direction of the display panel 14, and also is a thickness direction of the front panel 22.

Figure 3:
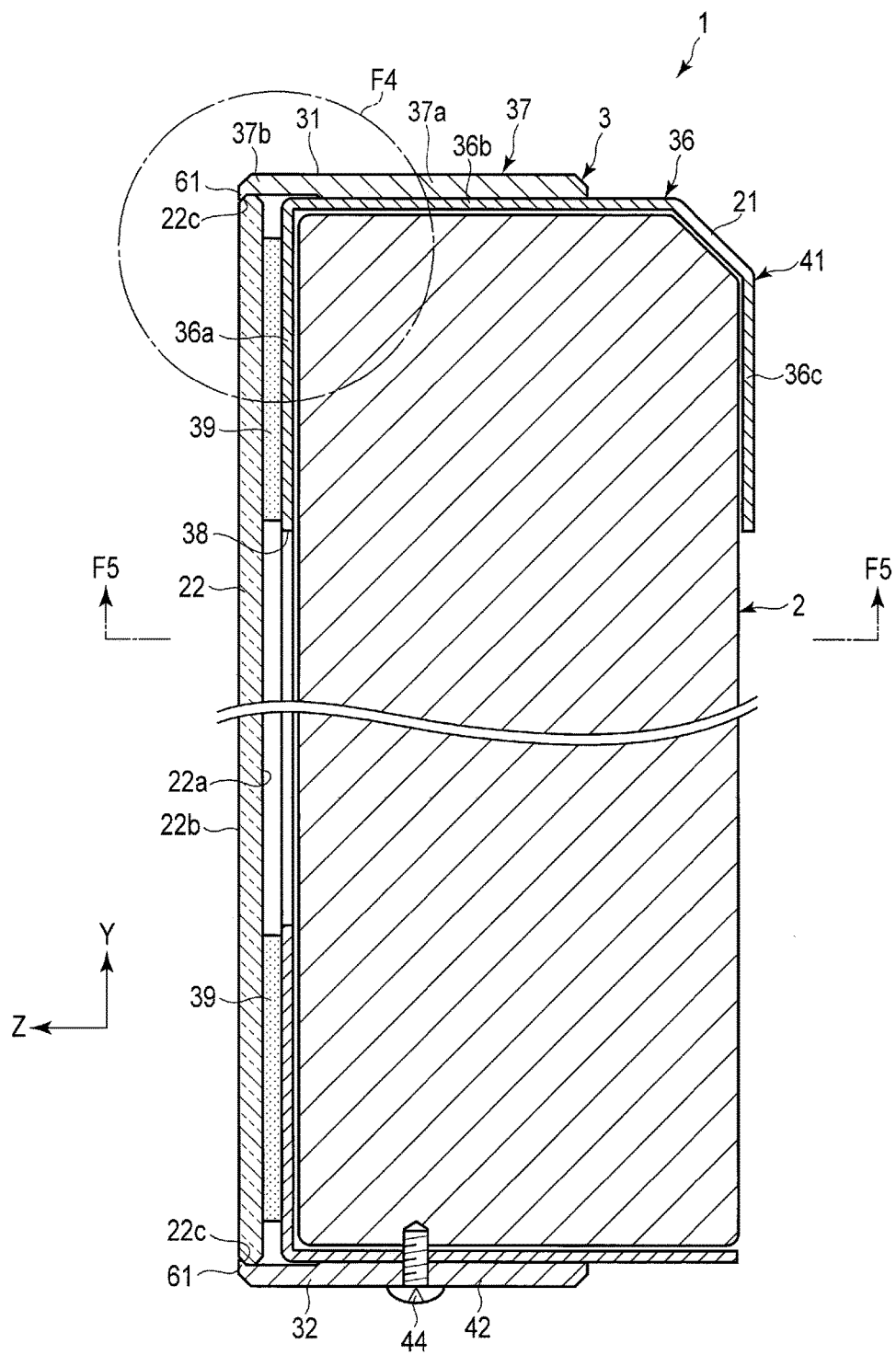
FIG. 3 is a cross-sectional view taken along line F3-F3 of the video display unit shown in FIG. 1.

As shown in FIG. 3, the frame 21 according to the present embodiment is composed of a first component 36 (base), a second component 37 (front panel supporting frame) mounted on the first component 36. The first component 36 comprises a first portion 36a, a second portion 36b, and a third portion 36c.

The first portion 36a is located forward of the housing 11 of the video display apparatus 2, and extends in a substantially vertical direction (first direction X). The first portion 36a faces a peripheral end of the front surface of the housing 11. That is, the first portion 36a is formed in the shape of a frame facing an upper end, a lower end, a left end, and a right end of the front surface of the housing 11. The first portion 36a defines a first opening 38 through which the display screen 14a of the video display apparatus 2 is exposed to the outside.

The second portion 36b extends backward from a peripheral edge of the first portion 36a. The second portion 36b extends along a peripheral surface of the housing 11 of the video display apparatus 2 in a substantially horizontal direction (third direction Z). That is, the second portion 36b is formed in the shape of a frame surrounding a top surface, a bottom surface, a left side surface, and a right side surface of the housing 11.

The third portion 36c extends downward from a back edge of the second portion 36b, for example, along an outer shape of the housing 11 of the video display apparatus 2. The third portion 36c is formed, for example, in the shape of a reverse U facing an upper end, a left end, and a right end of the back surface of the housing 11. It should be noted that the third portion 36c may also be formed in the shape of a frame facing the upper end, a lower end, the left end, and the right end of the back surface of the housing 11.

By the above-described structure, an upper end, a left end, and a right end of the housing 11 are sandwiched between the first portion 36a and the third portion 36c of the frame 21. The position of the protective cover 3 with respect to the housing 11 in the third direction Z is thereby fixed. In addition, the housing 11 is sandwiched between the second portion 36b located on the third side 33 of the protective cover 3 and the second portion 36b located on the fourth side 34. The position of the protective cover 3 with respect to the housing 11 in the second direction Y is thereby fixed.

Next, the second component 37 will be described.

The second component 37 is mounted on an outer surface of the second portion 36b of the first component 36. The second component 37 is formed in the shape of a frame surrounding a peripheral surface of the first component 36. The second component 37 comprises a first portion 37a and a second portion 37b. The first portion 37a is laid on the second portion 36b of the first component 36, and extends along the second portion 36b of the first component 36. The second portion 37b of the second component 37 further extends forward from the first portion 37a, and projects more forward than the first portion 36a of the first component 36.

As shown in FIG. 3, the front panel 22 is located forward of the display screen 14a of the display 13, and covers the display screen 14a. The front panel 22 is larger than the first opening 38 formed by the first portion 36a of the first component 36 of the protective cover 3. Thus, the front panel 22 faces the first opening 38, and also faces the first portion 36a of the first component 36.

The front panel 22 comprises a first surface 22a and a second surface 22b. The first surface 22a faces the display screen 14a of the display panel 14 and the first portion 36a of the first component 36. Between the first surface 22a and the first portion 36a of the first component 36, for example, an adhesive portion 39 (fixing portion) such as a double-sided tape or an adhesive is provided. The display panel 14 is fixed to the first portion 36a of the first component 36 by the adhesive portion 39. The second surface 22b is located on the opposite side to the first surface 22a, and extends substantially parallel to the first surface 22a. The second surface 22b is located on the outermost surface of the video display unit 1, and is exposed to the outside of the protective cover 3.

The front panel 22 is, for example, a glass plate, but is not limited to this, and may also be an acrylic plate, etc. As long as the front panel 22 is a panel having phototransmittance, functions and materials thereof are not particularly limited. The front panel 22 is, for example, a protective panel for protecting the display screen 14a of the display 13. The front panel 22 is not limited to a protective panel, but may also be, for example, a functional panel which polarizes or dims light radiated from the display screen 14a of the display 13. An example of the front panel 22 may also be a panel which realizes a 3D function of causing an image displayed on the display screen 14a of the display 13 to be viewed stereoscopically by a user (naked-eye 3D function). That is, a "cover mounted on a video display apparatus" to which the present embodiment is applied is not limited to a protective cover, but may also be a functional cover which offers various optical functions, or a cover used for other purposes.

Next, the structure of the protective cover 3 will be described from another viewpoint.

As shown in FIG. 2, the protective cover 3 can be decomposed into a main body portion 41 (cover main body) and a bottom cover 42. The main body portion 41 includes all of the first side 31, all of the third side 33, all of the fourth side 34, and the first portion 36a of the first component 36 located on the second side 32, of the frame 21, and the front panel 22. The main body portion 41 is thereby formed in the shape of a box which is opened downward and backward. The main body portion 41 can cover the housing 11 of the video display apparatus 2 from above.

On the other hand, the bottom cover 42 comprises the second portion 36b of the first component 36 located on the second side 32 of the frame 21, a pair of fixing portions 42a provided on the second portion 36b, and the first portion 37a and the second portion 37b of the second component 37 located on the second side 32. The bottom cover 42 is mounted on the main body portion 41 with the housing 11 of the video display apparatus 2 covered by the main body portion 41, and closes the bottom of the main body portion 41.

The pair of fixing portions 42a abuts an inner surface of the second portion 36b on the third side 33 and the inner surface of the second portion 36b on the fourth side 34 of the main body portion 41. The second portion 36b on the third side 33 and the second portion 36b on the fourth side 34 are provided with holes facing the fixing portions 42a. The bottom cover 42 can be fixed to the main body portion 41 by mounting first fixings 43 (for example, screws) to the fixing portions 42a through the holes.

Moreover, the second portion 36b of the bottom cover 42 is provided with holes facing the bottom surface of the housing 11 of the video display apparatus 2. The bottom cover 42 can be fixed to the housing 11 by mounting second fixings 44 (for example, screws) to the bottom surface of the housing 11 through the holes.

Next, the support structure of the front panel 22 will be described.

As shown in FIG. 2, the front panel 22 is formed in a rectangle, and comprises a first side 51, a second side 52, a third side 53, and a fourth side 54. The first side 51 is located at an upper end of the front panel 22, and extends in a substantially horizontal direction. The second side 52 is located at a lower end of the front panel 22, and extends substantially parallel to the first side 51. That is, the first side 51 and the second side 52 are two sides facing each other. The third side 53 is located at a left end of the front panel 22. The fourth side 54 is located at a right end of the front panel 22. The third side 53 and the fourth side 54 extend in a direction orthogonal to the first side 51 and the second side 52, and connect the first side 51 and the second side 52.

FIG. 4 shows the upper end of the front panel 22. The upper end of the front panel 22 comprises a locking surface 22c, a side surface 22d, a back slope 22e. The locking surface 22c is a recessed surface which is located inward (that is, backward) of the second surface 22b in the thickness direction of the display panel 14. In the present embodiment, the locking surface 22c is a slope inclined with respect to the second surface 22b, and extends backward from an edge of the second surface 22b. An example of the locking surface 22c is a so-called chamfered surface (C surface). The locking surface 22c is inclined, for example, substantially 45 degrees with respect to the second surface 22b.

The locking surface 22c is provided along at least one side of the second surface 22b. As shown in FIG. 3, in the present embodiment, the locking surface 22c is provided along each of the first side 51 and the second side 52 of the front panel 22. The locking surface 22c is formed, for example, substantially over the total lengths of the first side 51 and the second side 52. In addition, the locking surface 22c has, for example, substantially one third the thickness of the front panel 22 in the thickness direction of the front panel 22. It should be noted that the angle and the size of the locking surface 22c are not limited to the above-described examples.

The side surface 22d extends backward from a back edge of the locking surface 22c. In other words, the locking surface 22c extends slantingly between the second surface 22b and the side surface 22d. The side surface 22d is located at the outermost periphery of the front panel 22, and extends in a direction substantially orthogonal to the second surface 22b.

The back slope 22e extends from a back edge of the side surface 22d, being inclined toward the center of the front panel 22. The back slope 22e is substantially the same chamfered surface as the locking surface 22c, and is inclined, for example, substantially 45 degrees with respect to the second surface 22b. In other words, the back slope 22e extends slantingly between the side surface 22d and the first surface 22a.

As shown in FIG. 4, the second portion 37b of the protective cover 3 is a frame portion formed in the shape of a frame surrounding the peripheries (top, bottom, left, and right) of the front panel 22 and the adhesive portion 39. The second portion 37b of the protective cover 3 contacts the side surface 22d of the front panel 22, and supports the side surface 22d.

As shown in FIG. 3 and FIG. 4, the second portion 37b of the protective cover 3 comprises a support portion 61 which can support the locking surface 22c of the front panel 22. In the present embodiment, the support portion 61 extends along each of the first side 51 and the second side 52 of the front panel 22. In other words, one support portion 61 is provided at the main body portion 41, and the other support portion 61 is provided at the bottom cover 42.

The support portion 61 is located more forward than the locking surface 22c, and faces the locking surface 22c from the outside in the thickness direction of the display panel 14. The support portion 61 engages with the locking surface 22c when the front panel 22 moves forward, and restrains the front panel 22 from moving forward beyond the support portion 61. The support portion 61 is provided outside an area facing the second surface 22b in the thickness direction of the display panel 14.

The support portion 61 may contact the locking surface 22c, or a gap may exist between the support portion 61 and the locking surface 22c because of a tolerance of components, a flexure of the adhesive portion 39, etc. It suffices if the support portion 61 supports the locking surface 22c by contacting the locking surface 22c at least when the front panel 22 is about to move forward. In addition, between the support portion 61 and the locking surface 22c, for example, a cushion member (elastic member) such as rubber may be inserted.

In the present embodiment, the support portion 61 comprises a slope 61a extending substantially parallel to the locking surface 22c and facing the locking surface 22c. Specifically, the second component 37 of the protective cover 3 comprises a recess 62 recessed in the first direction X. The recess 62 is provided, for example, from the first portion 37a to the second portion 37b. The recess 62 is formed by, for example, a cutting process performed with a cutting tool such as an end mill. The recess 62 including the slope 61a is formed by the tip shape of this cutting tool.

As shown in FIG. 4, the second portion 37b of the second component 37 of the protective cover 3 comprises a front surface 64 exposed forward of the protective cover 3 in the thickness direction of the display panel 14. The protective cover 3 according to the present embodiment has a so-called full flush or full flat appearance, and the second surface 22b of the front panel 22 is located on the forefront surface of the protective cover 3 and occupies most of the forefront surface. The front surface 64 of the protective cover 3 is located on substantially the same plane as the second surface 22b of the front panel 22. In this specification, the phrase "on substantially the same plane" also means that the second surface 22b of the front panel 22 is located to be slightly shifted more backward than the front surface 64 of the protective cover 3 because of a tolerance of components, a flexure of the adhesive portion 39, etc.

Next, the peripheries of the left end and the right end of the front panel 22 will be described.

FIG. 5 shows the left end of the front panel 22. The left end of the front panel 22 comprises a slope 22f, the side surface 22d, and the back slope 22e. The slope 22f is a slope extending from the edge of the second surface 22b, being inclined backward with respect to the second surface 22b. The slope 22f is substantially the same chamfered surface (C surface) as the locking surface 22c, and is inclined substantially 45 degrees with respect to the second surface 22b. The slope 22f is provided, for example, substantially over the total lengths of the third side 53 and the fourth side 54. As shown in FIG. 6, a width W2 of the slope 22f is substantially the same as a width W1 of the locking surface 22c.

As shown in FIG. 5, the support portion 61 is not provided on the third side 33 and the fourth side 34 of the protective cover 3. Gaps g are provided between the third side 33 of the protective cover 3 and the side surface 22d of the front panel 22 and between the fourth side 34 and the side surface 22d of the front panel 22.

In other words, the protective cover 3 has the following structure.

As shown in FIG. 5 and FIG. 6, the second component 37 of the protective cover 3 comprises a second opening 65 through which the second surface 22b of the front panel 22 is exposed to the outside. The gaps g are provided between an inner edge of the second opening 65 and the third side 53 of the front panel 22, and between the inner edge of the second opening 65 and the fourth side 54 of the front panel 22. Thus, as shown in FIG. 6, a width S1 of the locking surface 22c exposed through the second opening 65 is less (narrower) than a width S2 of the slope 22f exposed through the second opening 65. In the present embodiment, since the slope 22f is not covered by the support portion 61, the width S2 of the slope 22f exposed through the second opening 65 corresponds to the width W2 of the slope 22f.

As shown in FIG. 5, in the protective cover 3, a facing member 67 may be inserted in the gap g between the inner edge of the second opening 65 and the third side 53 of the front panel 22, and the gap g between the inner edge of the second opening 65 and the fourth side 54 of the front panel 22. The facing member 67 is an example of an "infilling member". The facing member 67 may comprise, for example, a projection 67a facing the slope 22f from the outside in the thickness direction of the display panel 14.

Next, an assembling method of the protective cover 3 will be described.

As shown in FIG. 7, before the front panel 22 is mounted, the first component 36 and the second component 37 are fixed to each other by, for example, welding. In addition, the adhesive portion 39 is provided on the first portion 36a of the first component 36. It should be noted that the adhesive portion 39 may be provided on the first surface 22a of the front panel 22 instead of being provided on the first portion 36a of the first component 36. Further, the bottom cover 42 is not mounted on the main body portion 41 yet.

Figure 8:
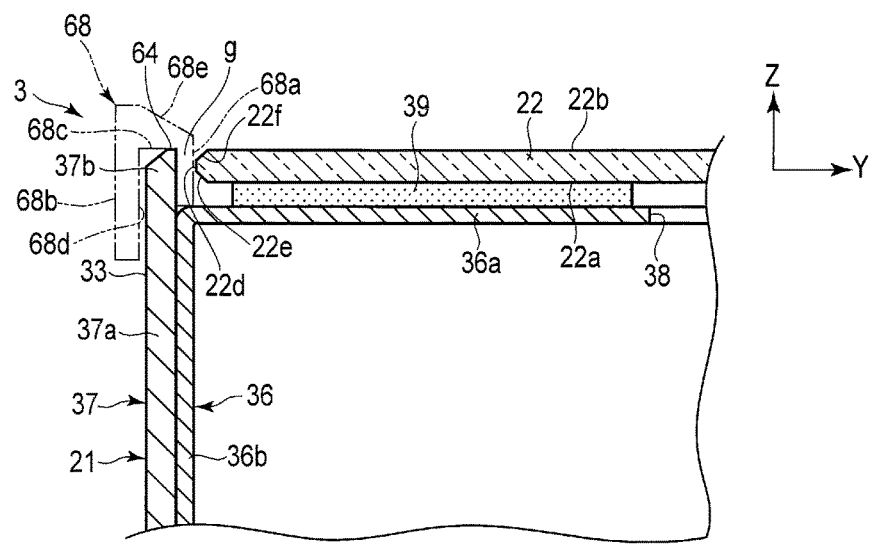
FIG. 8 is a cross-sectional view illustrating the example of the assembling method of the protective cover shown in FIG. 1.

The front panel 22 is slantingly inserted in the recess 62 of the first component 36 of the protective cover 3. At this time, as shown in FIG. 8, a jig 68 may be mounted in the gap g between the inner edge of the second opening 65 and the third side 53 of the front panel 22, and the gap g between the inner edge of the second opening 65 and the fourth side 54 of the front panel 22 so that the sliding of the front panel 22 is guided by the jig 68. The front panel 22 can be smoothly inserted in the recess 62 by, for example, abutting the jig 68. In addition, the front panel 22 is made horizontal with the side surface 22d of the first side 51 of the front panel 22 stuck in the recess 62, and the frame 21 and the front panel 22 are fixed by the adhesive portion 39.

As shown in FIG. 8, an example of the jig 68 comprises a first portion 68a, a second portion 68b, and a third portion 68c. Here, the top and the bottom are defined with respect to the state where the front panel 22 is mounted (state where the first portion 36a of the first component 36 is laid to be substantially horizontal).

The first portion 68a is inserted in the gap g between the inner edge of the second opening 65 and the third side 53 of the front panel 22, or the gap g between the inner edge of the second opening 65 and the fourth side 54 of the front panel 22. The front panel 22 can thereby slide, being guided by the first portion 68a.

The second portion 68b is located outside the frame 21, and faces an outer surface of the frame 21. The second portion 68b extends substantially parallel to the first portion 68a in a substantially vertical direction (thickness direction of the protective cover 3). The second portion 68b extends more upward than the first portion 68a, and extends more downward than the first portion 68a.

The third portion 68c extends in a direction intersecting with the first portion 68a, and connects an end of the first portion 68a and an end of the second portion 68b. The jig 68 thereby comprises a depression 68d by which the second portion 37b of the second component 37 can be covered from above. The second portion 37b of the second component 37 is covered by the depression 68d, whereby the jig 68 is stably supported by the second component 37.

A top surface of the third portion 68c comprises a slope 68e. The slope 68e is inclined to be more downward as it extends from the second portion 68b to the first portion 68a. When the slope 68e like this is provided, the front panel 22 can easily abut the first portion 68a. The shape of the jig 68 is not limited to the above-described example, but various shapes can be adopted as appropriate.

After the front panel 22 is fixed to the frame 21 by the adhesive portion 39, the housing 11 of the video display apparatus 2 is covered by the main body portion 41. Finally, the bottom cover 42 is mounted on the main body portion 41 from below. At this time, the front panel 22 is sandwiched between the support portion 61 of the main body portion 41 (the support portion 61 of the first side 31) and the support portion 61 of the bottom cover 42 (the support portion 61 of the second side 32). Both the upper and lower ends of the front panel 22 are thereby prevented from coming out of the frame 21.

Next, a phototransmissive portion 71 of the protective cover 3 will be described.

As shown in FIG. 1 and FIG. 2, the front surface of the housing 11 of the video display apparatus 2 is provided with a light-emitting portion (indicator). The light-emitting portion 72 includes, for example, an LED element, and is turned on or off in accordance with the state (for example, power is on/off) of the video display apparatus 2. The phototransmissive portion 71 is provided on a front surface of the protective cover 3, and faces the light-emitting portion 72 of the video display apparatus 2. A user can check the state of the light-emitting portion 72 through the phototransmissive portion 71.

In the present embodiment, the first surface 22a of the front panel 22 is provided with a printing layer 73 (coating layer) whose region facing the first portion 36a of the first component 36 is in a first color (for example, black). The phototransmissive portion 71 according to the present embodiment is not transparent, and is provided with a printing layer 73 (coating layer) in a second color (for example, light black) which is, for example, the same type of color as the above first color and translucent. That is, an example of the second color is a translucent color obtained by diluting the first color. The second color is, for example, a mixture of an ink used for the first color and a transparent ink in a predetermined ratio.

Here, if the phototransmissive portion 71 is transparent, the periphery of the light-emitting portion 72 will be seen well by a user through the phototransmissive portion 71 when the light-emitting portion 72 is turned off, and the deterioration of the design of the video display unit 1 is also assumed.

On the other hand, according to the phototransmissive portion 71 as disclosed in the present embodiment, even when the light-emitting portion 72 is turned off, the periphery of the light-emitting portion 72 is hardly seen through the phototransmissive portion 71. Thus, the design of the video display unit 1 can be improved. The second color need not be the same type of color as the first color, and may also be a color obtained by making a color differing from the first color translucent.

According to the video display unit 1 having the above-described structure, the reliability can be improved.

In recent years, the design of a narrow frame has been the mainstream design of video apparatuses such as monitors. Above all, a design having no concept of a frame from the beginning in which one sheet of glass is mounted on a front surface of a screen (so-called full flush) has been proposed.

For example, an electronic apparatus in the full flush design is not provided with a frame supporting glass, and thus, the strength of fixing of glass depends on its strength of adhesion. Although the strength of adhesion of glass is sufficiently examined at the time of manufacturing, there is a possibility that an adhesive (or an adhesive tape) will deteriorate and glass will come out, for example, when being used for a long time in an environment not intended by a maker, for example, an environment of constant exposure of rain, wind and snow, and an environment at extremely low or high temperature. This possibility may increase more, when the area of attachment decreases because of a future progress in the narrowing of a frame.

Therefore, in the present embodiment, the front panel 22 comprises the first surface 22a facing the display screen 14a, the second surface 22b which is located on the opposite side to the first surface 22a and is exposed to the outside, and the locking surface 22c which is provided along at least one side of the second surface 22b and is located inward of the second surface 22b in the protective cover 3 in the thickness direction of the display panel 14. The protective cover 3 comprises the support portion 61 facing the locking surface 22c from the outside in the thickness direction of the display panel 14.

According to such a structure, the front panel 22 is mechanically fixed while the design is maintained, and the possibility that the front panel 22 will come out can be more surely eliminated. The safety of the video display unit 1 is thereby more increased, and the reliability can be improved.

The protective cover 3 according to the present embodiment can be used in, for example, a medical scene as one of uses. In the medical scene, the video display apparatus 2 having a 3D function (naked-eye 3D function) is sometimes used to view, for example, the conditions and analysis results of the brain and the organs stereoscopically. In the video display apparatus 2 like this, the display screen 14a of the display panel 14 (display cell) has projections and depressions, and when dirt and dust adhere to the projections and depressions, part of images may be disturbed. In addition, in the medical scene, it is also assumed that the video display apparatus 2 is used in a place surrounded by liquids such as various chemicals.

In such an environment, dirt and dust can be restrained from adhering to the display screen 14a of the video display apparatus 2 by mounting the protective cover 3 on the video display apparatus 2, whereby clear images can be maintained. In addition, the video display apparatus 2 can be protected from liquids such as chemicals by mounting the protective cover 3 on the video display apparatus 2. Thus, in the medical scene, there are various advantages in mounting the protective cover 3 on the video display apparatus 2.

That is, the video display unit 1 according to the present embodiment can be used as an example of a medical monitor which can display, for example, medical stereoscopic images. In this case, stereoscopic images may be directly displayed on the display panel 14, or may be displayed by a combination of the display panel 14 and the front panel 22 having an optical function.

In the present embodiment, the support portion 61 is provided outside the region facing the second surface 22b in the thickness direction of the display panel 14. According to such a structure, the second surface 22b of the front panel 22 is not covered by the support portion 61, and thus, the design of the video display unit 1 can be further improved.

In the present embodiment, the locking surface 22c is a slope extending from the edge of the second surface 22b, being inclined with respect to the second surface 22b. The support portion comprises the slope 61a extending substantially parallel to the locking surface 22c. According to such a structure, the processing operation of the edge of the front panel 22 necessary to form the locking surface 22c can be simplified. The manufacturing cost of the video display unit 1 can be thereby reduced.

In the present embodiment, the protective cover 3 comprises the front surface 64 exposed forward of the protective cover 3 in the thickness direction of the display panel 14. The second surface 22b of the front panel 22 and the front surface 64 of the protective cover 3 are located on substantially the same plane. According to such a structure, the front panel 22 can be mechanically fixed in a so-called full flush structure, whereby the design of the video display unit 1 can be further improved.

In the present embodiment, the front panel 22 is formed in a rectangle, and comprises the first side 51 and the second side 52 facing each other. The locking surface 22c is provided along each of the first side 51 and the second side 52. The protective cover 3 comprises the support portion 61 at each portion adjacent to the first side 51 and the second side 52. According to such a structure, both sides of the front panel 22 are fixed by the support portion 61, and the front panel 22 more hardly comes out of the frame 21. The reliability of the video display unit 1 can be thereby further improved.

In the present embodiment, the front panel 22 comprises the third side 53 and the fourth side 54 extending between the first side 51 and the second side 52. The protective cover 3 comprises the opening 65 through which the second surface 22b of the front panel 22 is exposed. The gaps g are provided between the inner edge of the opening 65 and the third side 53 of the front panel 22, and between the inner edge of the opening 65 and the fourth side 54 of the front panel 22. According to such a structure, the front panel 22 can be more smoothly inserted in the protective frame 21 comprising the support portion 61. The assembly of the protective cover 3 can be thereby improved. In addition, in an example, the jig 68 can be attached by using these gaps g. The assembly of the protective cover 3 can be thereby further improved.

In the present embodiment, the front panel 22 comprises the slope 22f having substantially the same width as the locking surface 22c on the third side 53 and the fourth side 54. The width S1 of the locking surface 22c exposed through the opening 65 is less than the width S2 of the slope 22f of the third side 53 exposed through the opening 65. That is, since the support portion 61 faces the locking surface 22c from the outside, the width S1 of the locking surface 22c exposed through the opening 65 is necessarily less than the width S2 of the slope 22f of the third side 53 exposed through the opening 65. Thus, according to the above-described structure, it can be easily checked by comparing the width S1 of the locking surface 22c exposed through the opening 65 and the width S2 of the slope 22f of the third side 53 exposed through the opening 65 that the support portion 61 functions (the support portion 61 engages with the locking surface 22c). The reliability of the video display unit 1 can be thereby further improved.

In the present embodiment, the facing member (infilling member) is inserted in each of the gap g between the inner edge of the opening 65 and the third side 53 of the front panel 22, and the gap g between the inner edge of the opening 65 and the fourth side 54 of the front panel 22. According to such a structure, these gaps g can be hidden from the outside. The attractiveness of the appearance of the video display unit 1 can be thereby further improved.

In the present embodiment, the facing member 67 has the projection 67a facing the slope 22f of the third side 53 or the fourth side 54 from the outside in the thickness direction of the display panel 14. According to such a structure, the width S1 of the locking surface 22c exposed through the opening 65 and the width S2 of the slope 22f of the third side 53 and the fourth side 54 exposed through the opening 65 can be made substantially the same. The design of the video display unit 1 can be thereby further improved.

Next, the video display unit 1 according to first to third modifications will be described.

First Modification

Figure 9:
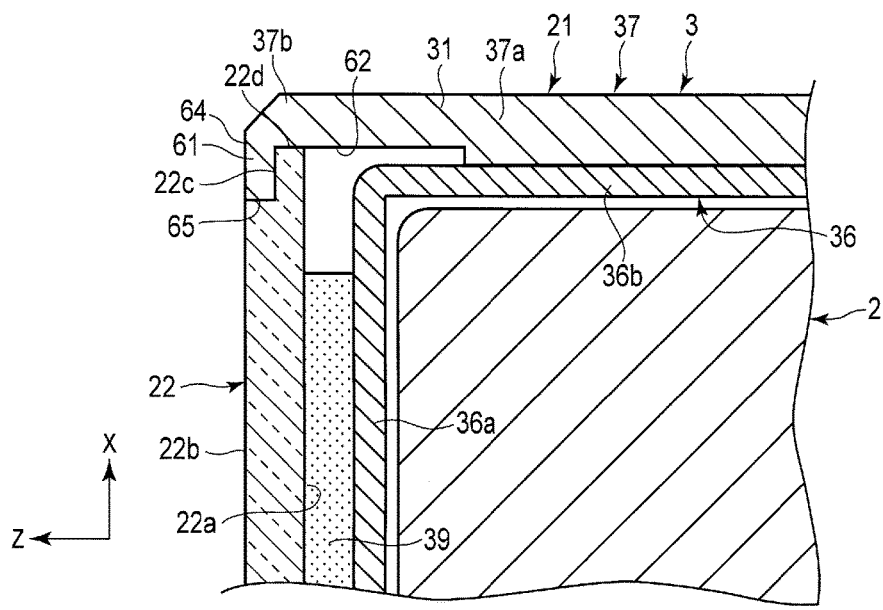
FIG. 9 is a cross-sectional view illustrating the protective cover according to a first modification of the first embodiment.

FIG. 9 shows the video display unit 1 according to the first modification of the first embodiment. In the present modification, the locking surface 22c comprises a step on the second surface 22b, and extends substantially parallel to the second surface 22b. The support portion 61 includes a plane which extends substantially parallel to the locking surface 22c and faces the locking surface 22c. Also according to such a structure, the reliability of the video display unit 1 can be improved as in the above-described first embodiment. It should be noted that the cost for forming the locking surface 22c in the shape of a slope according to the above-described first embodiment can be more reduced than in the present modification.

Second Modification

Figure 10:
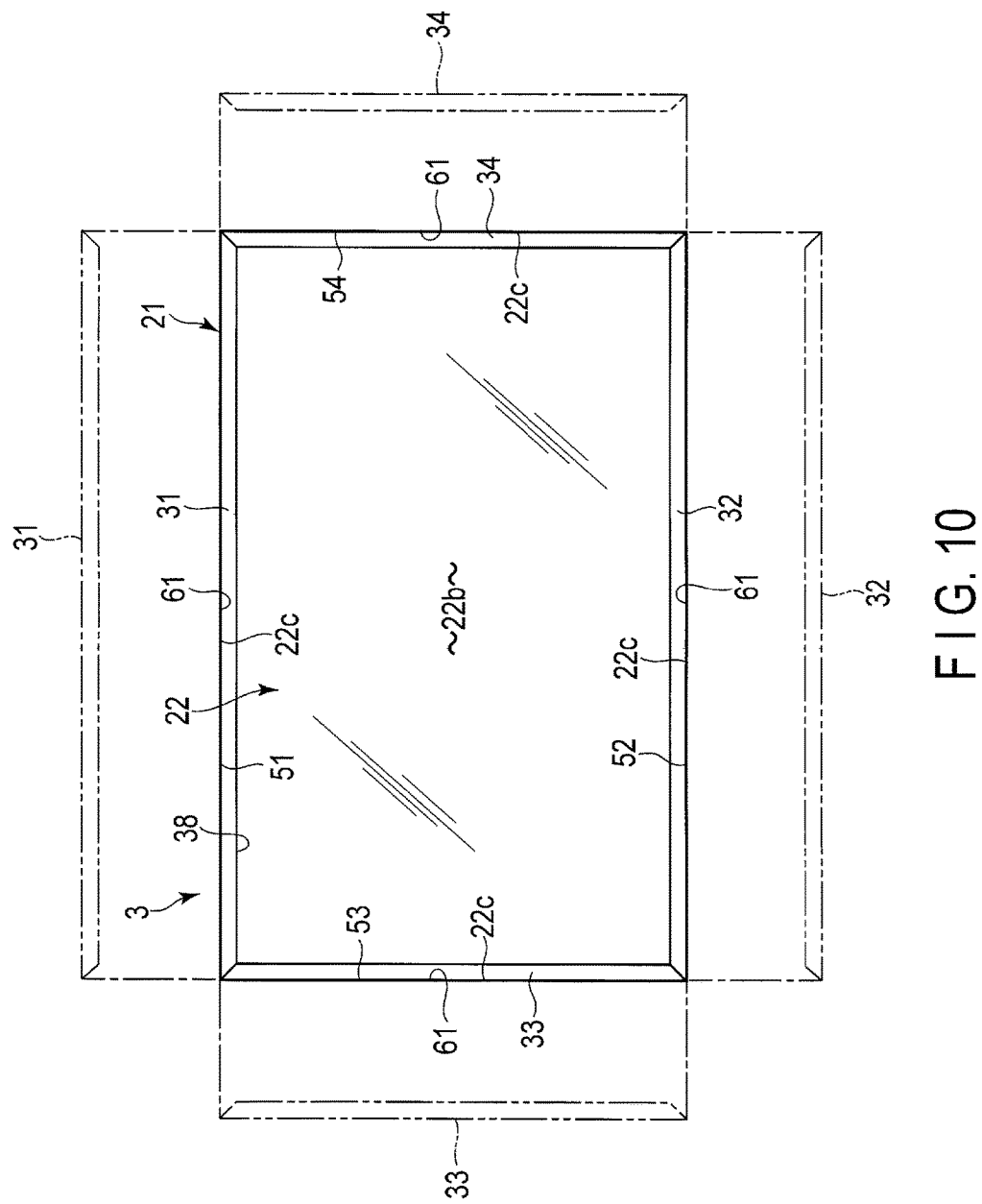
FIG. 10 is a front view illustrating the protective cover according to a second modification of the first embodiment.

FIG. 10 shows the video display unit 1 according to the second modification of the first embodiment. In the present modification, the locking surface 22c is provided along each of the four sides 51, 52, 53 and 54 of the front panel 22. The protective cover 3 comprises the support portion 61 at each portion adjacent to the four sides 51, 52, 53 and 54 of the front panel 22.

In the present modification, the first side 31, the second side 32, the third side 33, and the fourth side 34 of the frame 21 are detachable from each other. That is, the frame 21 is composed of a combination of the first side 31, the second side 32, the third side 33, and the fourth side 34, which are formed separately from each other.

Also according to such a structure, the reliability of the video display unit 1 can be improved as in the above-described first embodiment. In addition, since the first side 31, the second side 32, the third side 33, and the fourth side 34 are formed to be detachable from each other, the front panel 22 can be easily put in the frame 21 comprising the support portion 61 on its periphery.

Third Modification

FIG. 11 shows the video display unit 1 according to the third modification of the first embodiment. In the present modification, a film 81 is stuck on the second surface 22b of the front panel 22. The film 81 is, for example, an optical film which polarizes and dims light radiated from the display screen 14a of the display panel 14, and an example thereof is an antiglare film which restrains glare. It should be noted that the film 81 may also be, for example, a touch sensor film which offers a touch input function to the video display unit 1.

The film 81 is located in the region of the second surface 22b outside the locking surface 22c. That is, the film 81 does not overlap with the locking surface 22c in the thickness direction of the display panel 14. In this case, the full flat design can be achieved by, for example, thinning the front panel 22 by the thickness of the film 81.

Also according to such a structure, the reliability of the video display unit 1 can be improved as in the above-described first embodiment. Moreover, according to the present embodiment, the front panel 22 can be mechanically fixed also in the structure in which the front panel 22 comprises the film 81.

In the structure shown in FIG. 11, the two chamfered surfaces (the locking surface 22c and the back slope 22e) of the front panel 22 are substantially the same in size. According to such a structure, the designing can be made easier.

FIG. 12 shows a further modification related to the present modification. In the structure shown in FIG. 12, the two chamfered surfaces (the locking surface 22c and the back slope 22e) of the front panel 22 differ in size. Specifically, the size of the locking surface 22c is less than the size of the back slope 22e. The thickness of the front panel 22 is, for example, substantially the same as the thickness of the front panel 22 shown in FIG. 4.

Such a structure is useful, for example, in realizing the full flat design comprising the film 81 without changing the thickness of the front panel 22 and the size of the back slope 22e from those in the structure not comprising the film 81 as shown in FIG. 4.

In addition, the chamfered surfaces (the locking surface 22c and the back slope 22e) of the front panel 22 are, for example, less than or equal to 1 mm, and minute processing is required. Here, in the present embodiment, the size of the back slope 22e is greater than the size of the locking surface 22c. According to such a structure, the processing of the locking surface 22c can be performed with high precision while the processing of the back slope 22e is performed with a little lower precision. That is, the number of surfaces which require precision can be reduced by enlarging the size of the back slope 22e, which has an allowance in dimensions, and the productivity of the front panel 22 can be thereby increased.

It should be noted that the film 81 may also be located more forward than the front surface 64 as shown in FIG. 13, although it is not strictly a full flat design.

Next, electronic apparatuses 91 and a video display unit 101 according to second to fifth embodiments will be described. Of the structures of the first to fifth embodiments, structures having the same or similar functions as or to each other will be given the same numbers and detailed explanations thereof will be omitted. Moreover, in each of the embodiments, structures other than those described hereinafter are the same as in the first embodiment.

Second Embodiment

Figure 14:
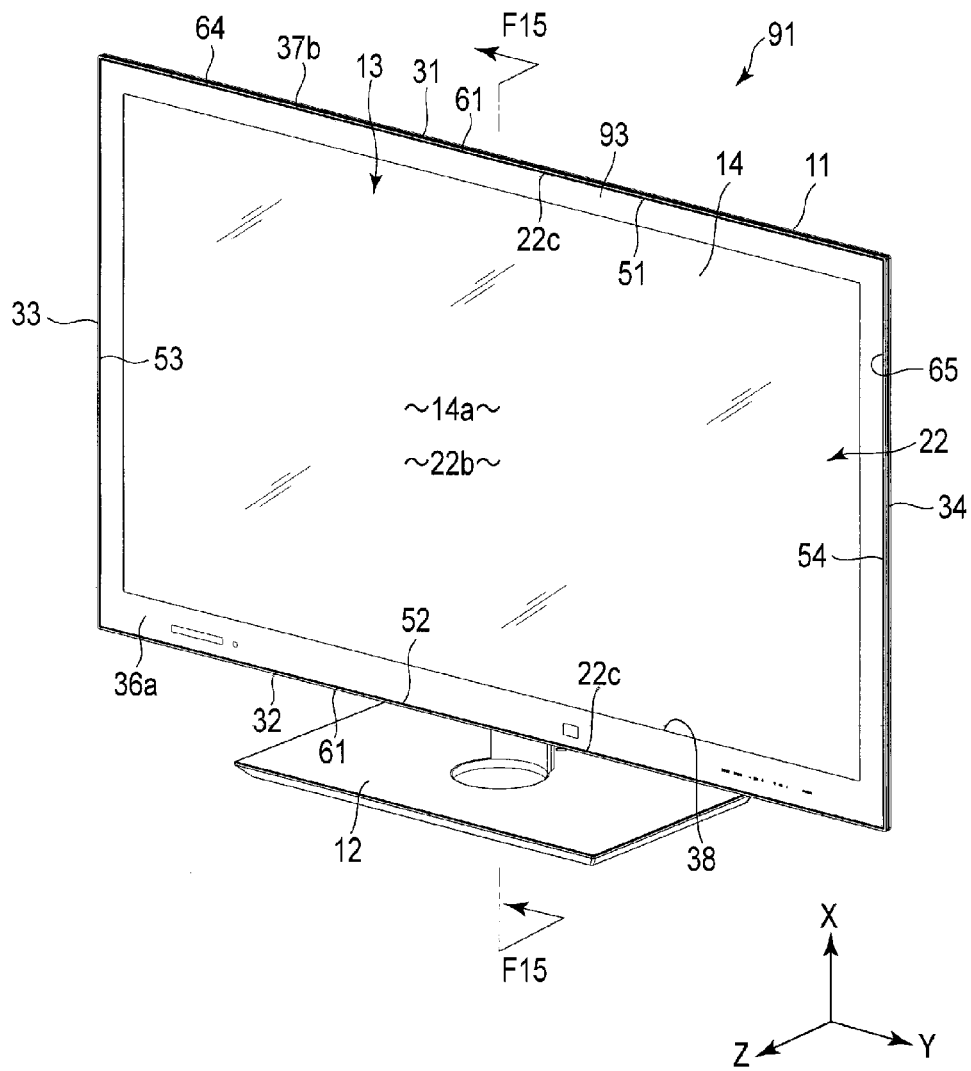
FIG. 14 is a perspective view illustrating a television receiver according to a second embodiment.

FIG. 14 and FIG. 15 show the electronic apparatus 91 according to the second embodiment. As shown in FIG. 14, the electronic apparatus 91 is, for example, a television receiver. It should be noted that the present embodiment is applicable not only to the above-described electronic apparatus, but is widely applicable to various electronic apparatuses such as digital signage, tablet terminals (multifunctional portable terminals), smartphones, and monitors. In addition, the electronic apparatus 91 can also be used as, for example, a medical monitor which can display medical stereoscopic images. In this case, stereoscopic images may be directly displayed on a display panel 14, or may be displayed by a combination of the display panel 14 and a front panel 22 having an optical function.

As shown in FIG. 14, the electronic apparatus 91 comprises a housing 11 and a stand 12. The housing 11 is held by the stand 12, and is supported in a vertical attitude. The housing 11 is exposed to the outside of the electronic apparatus 91, and forms an outer surface (outer hull) of the electronic apparatus 91.

As shown in FIG. 14 and FIG. 15, the housing 11 accommodates a display 13. The display 13 is, for example, a liquid crystal display, and comprises the display panel 14 (liquid crystal panel), a backlight unit 92, a front bezel 93, a middle frame 94, and a back chassis 95. The display 13 is not limited to a liquid crystal display, but may also be, for example, a plasma display or an organic EL display. The display panel 14 includes a display screen 14a. The backlight unit 92 is located behind the display panel 14.

As shown in FIG. 15, the front bezel 93 comprises a first opening 38 through which the display screen 14a is exposed. The middle frame 94 is located between a peripheral end of the display panel 14 and a peripheral end of the backlight unit 92. The back chassis 95 is located behind the backlight unit 92. Thus, the peripheral end of the display panel 14 is held by the front bezel 93 and the middle frame 94, and the peripheral end of the backlight unit 92 is held by the middle frame 94 and the back chassis 95. Between the back chassis 95 and a back wall 96 of the housing 11, for example, circuit boards 97 are provided.

As shown in FIG. 15, the front panel 22 is located forward of the display screen 14a of the display 13, and covers the display screen 14a. The front panel 22 is greater than the first opening 38 formed by the front bezel 93 of the display 13. Thus, a first surface 22a of the front panel 22 faces the first opening 38, and faces a front surface of the front bezel 93. The front panel 22 is fixed to the front bezel 93 by an adhesive portion 39. A second surface 22b is located at the outermost portion of the electronic apparatus 91, and is exposed to the outside of the electronic apparatus 91.

As shown in FIG. 15, in the present embodiment, the housing 11 comprises a projection 37b projecting more forward than the front bezel 93 of the display 13. The projection 37b is formed in the shape of a frame surrounding the peripheries (top, bottom, left, and right) of the front panel 22 and the adhesive portion 39. The projection 37b includes the first side 31, the second side 32, the third side 33, and the fourth side 34. The projection 37b contacts a side surface 22d of the front panel 22 and supports the side surface 22d.

As shown in FIG. 15, the projection 37b of the housing 11 comprises a support portion 61 which can support a locking surface 22c of the front panel 22. In the present embodiment, the locking surface 22c and the support portion 61 are provided along each of a first side 51 and a second side 52. It should be noted that the locking surface 22c and the support portion 61 may also be provided along each of four sides 51, 52, 53, and 54.

As shown in FIG. 15, the projection 37b of the housing 11 comprises a front surface 64 exposed forward of the housing 11 in the thickness direction of the display panel 14. A protective cover 3 according to the present embodiment has a so-called full flush or full flat appearance, and the second surface 22b of the front panel 22 is located on the forefront surface of the housing 11 and occupies most of the forefront surface. In the present embodiment, the front surface 64 of the housing 11 is located on substantially the same plane as the second surface 22b of the front panel 22.

Third Embodiment

Figure 16:
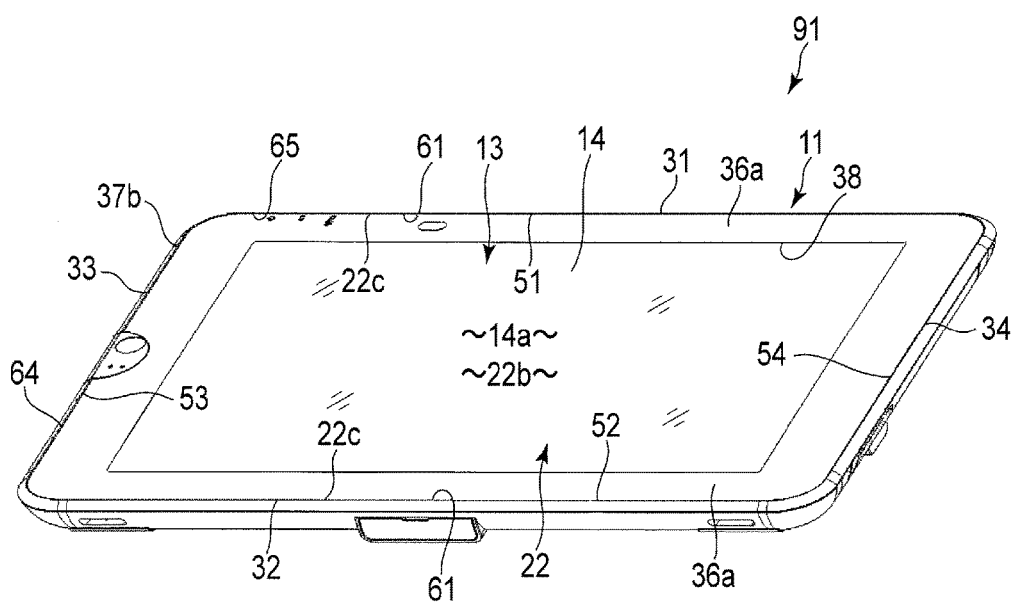
FIG. 16 is a perspective view illustrating a tablet terminal according to a third embodiment.

FIG. 16 shows the electronic apparatus 91 according to the third embodiment. As shown in FIG. 16, the electronic apparatus 91 is a tablet terminal (multifunctional portable terminal). In the present embodiment, a locking surface 22c and a support portion 61 are provided along each of a first side 51 and a second side 52. It should be noted that the locking surface 22c and the support portion 61 may also be provided along each of four sides 51, 52, 53 and 54 of a front panel 22.

Also according to such a structure, the reliability of the electronic apparatus 91 can be improved as in the above-described first and second embodiments.

Fourth Embodiment

FIG. 17 shows the electronic apparatus 91 according to the fourth embodiment. As shown in FIG. 17, the electronic apparatus 91 is a smartphone. In the present embodiment, a locking surface 22c and a support portion 61 are provided along each of a first side 51 and a second side 52. It should be noted that the locking surface 22c and the support portion 61 may also be provided along each of four sides 51, 52, 53 and 54 of a front panel 22.

Also according to such a structure, the reliability of the electronic apparatus 91 can be improved as in the above-described first and second embodiments.

Fifth Embodiment

FIG. 18 shows the video display unit 101 according to the fifth embodiment. The video display unit 101 is, for example, digital signage. It should be noted that the video display unit 101 may be a television receiver, a medical monitor, or other electronic apparatuses.

As shown in FIG. 18, the video display unit 101 includes a video display apparatus 2 and a protective cover 3. The video display apparatus 2 is used, for example, being mounted on a wall 102. The wall 102 is an example of an "installation location (installation portion) where a video display apparatus is installed". The "installation location where a video display apparatus is installed" is not limited to a wall, but is a ceiling, a floor, a television stand, or the like, as appropriate.

The video display apparatus 2 according to the present embodiment comprises a display unit 103 (display main body), and a wall-hung fitting 104 by which the display unit 103 is mounted on the wall 102. The wall-hung fitting 104 is an example of an "installation unit". The wall-hung fitting 104 is located between the display unit 103 and the wall 102, and supports the display unit 103.

The display unit 103 comprises a housing 11 and a display 13 (that is, a display panel 14 and a backlight unit 92) accommodated in the housing 11. A back chassis 95 (back cover) covers the back of the backlight unit 92. The back chassis 95 is fixed to the wall-hung fitting 104 with a back wall 96 of the housing 11, and is supported by the wall-hung fitting 104. The back wall 96 and the back chassis 95 of the housing 11 are fixed to the wall-hung fitting 104 by, for example, screws 105. The wall-hung fitting 104 is fixed to the wall 102.

As shown in FIG. 18, the protective cover 3 is mounted on the video display apparatus 2 as in the first embodiment. Details of the protective cover 3 are substantially the same as in the first embodiment.

Also according to such a structure, the reliability of the video display unit 101 can be improved as in the above-described first and second embodiments.

Next, the video display unit 101 according to first to third modifications will be described.

First Modification

FIG. 19 shows the video display unit 101 according to the first modification of the fifth embodiment. In the present modification, the wall-hung fitting 104 is provided with a shock absorber 106 (buffer). The shock absorber 106 includes, for example, an elastic material such as rubber and a spring, or a buffer member such as a hydraulic damper and an air damper.

The wall-hung fitting 104 is provided between the wall 102 and the display unit 103. The wall-hung fitting 104 comprises a first member 111 fixed to the wall 102, a second member 112 fixed to the display unit 103, and a third member 113 provided between the first member 111 and the second member 112. A lower end of the second member 112 is, for example rotatably, coupled to a lower end of the first member 111. The third member 113 extends between an upper end of the first member 111 and an upper end of the second member 112, and is rotatably coupled to each of the upper end of the first member 111 and the upper end of the second member 112. The third member 113 couples the first member 111 and the second member 112.

As shown in FIG. 19, in the present embodiment, the shock absorber 106 is provided between the lower end of the first member 111 and the lower end of the second member 112, and in a middle of the third member 113. Thus, part of shock and oscillation transmitted from the wall 102 to the first member 111 is absorbed by the shock absorber 106 before being transmitted to the display unit 103 and the protective cover 3. Large shock and oscillation are thereby hardly transmitted to the display unit 103 and the protective cover 3.

Second Modification

Figure 20:
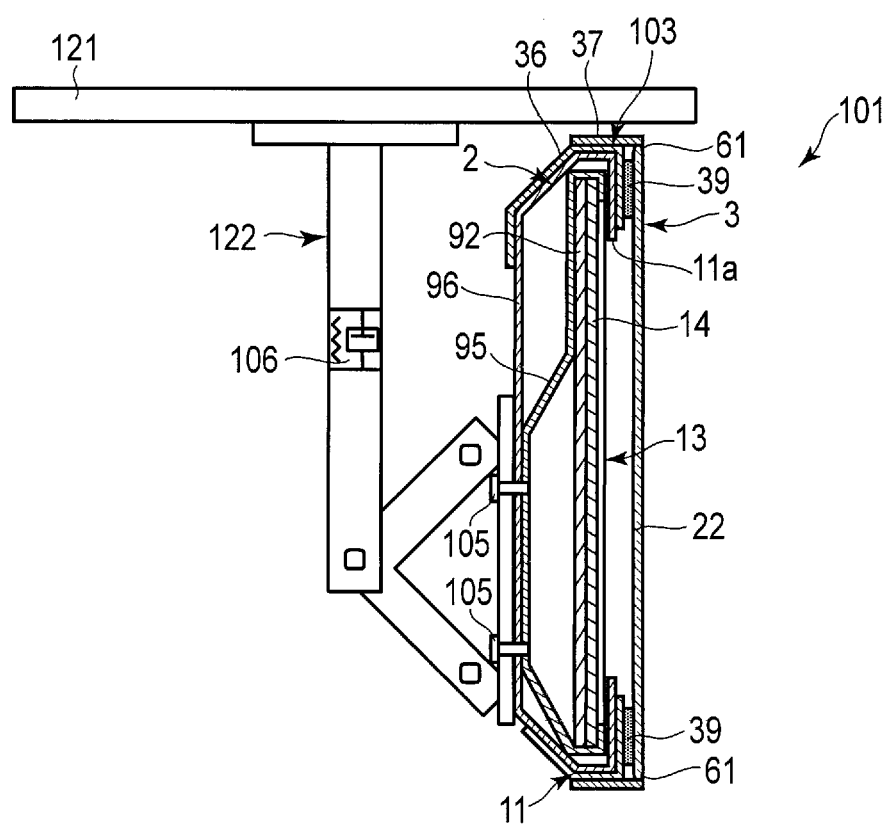
FIG. 20 is a cross-sectional view illustrating the video display unit according to a second modification of the fifth embodiment.

FIG. 20 shows the video display unit 101 according to the second modification of the fifth embodiment. In the present modification, the video display unit 101 includes the display unit 103 and a mounting member 122 by which the display unit 103 is mounted on a ceiling 121. The ceiling 121 is an example of an "installation location (installation portion) where a display is installed". The mounting member 122 is an example of an "installation unit", and is provided between the ceiling 121 and the display unit 103.

As shown in FIG. 20, in the present modification, the shock absorber 106 is provided in a middle of the mounting member 122. Thus, part of shock and oscillation transmitted from the ceiling 121 to the mounting member 122 is absorbed by the shock absorber 106 before being transmitted to the display unit 103 and the protective cover 3. Large shock and oscillation are thereby hardly transmitted to the display unit 103 and the protective cover 3.

Third Modification

FIG. 21 shows the video display unit 101 according to the third modification of the fifth embodiment. In the present modification, the video display unit 101 includes the display unit 103 and a stand 12 which supports the display unit 103 on a floor 125 (or a television stand). The floor 125 (or the television stand) is an example of the "installation location (installation portion) where a display is installed". The stand 12 is an example of the "installation unit", and is provided between the floor 125 and the display unit 103.

As shown in FIG. 21, in the present modification, the shock absorber 106 is provided in a middle of the stand 12. Thus, part of shock and oscillation transmitted from the floor 125 to the stand 12 is absorbed by the shock absorber 106 before being transmitted to the display unit 103 and the protective cover 3. Large shock and oscillation are thereby hardly transmitted to the display unit 103 and the protective cover 3.

Fourth Modification

FIG. 22 shows the video display unit 101 according to the fourth modification of the fifth embodiment. In the present modification, the stand 12 includes a stand main body 131 (installation unit main body) installed on the floor 125 and a mounting plate 132 mounted on the display unit 103. The mounting plate 132 is supported by the stand main body 131 (installation unit main body).

In the present modification, the shock absorber 106 is provided between the stand main body 131 and the mounting plate 132. Thus, part of shock and oscillation transmitted from the floor 125 to the stand 12 is absorbed by the shock absorber 106 before being transmitted to the display unit 103 and the protective cover 3. Large shock and oscillation are thereby hardly transmitted to the display unit 103 and the protective cover 3.

Fifth Modification

Figure 23:
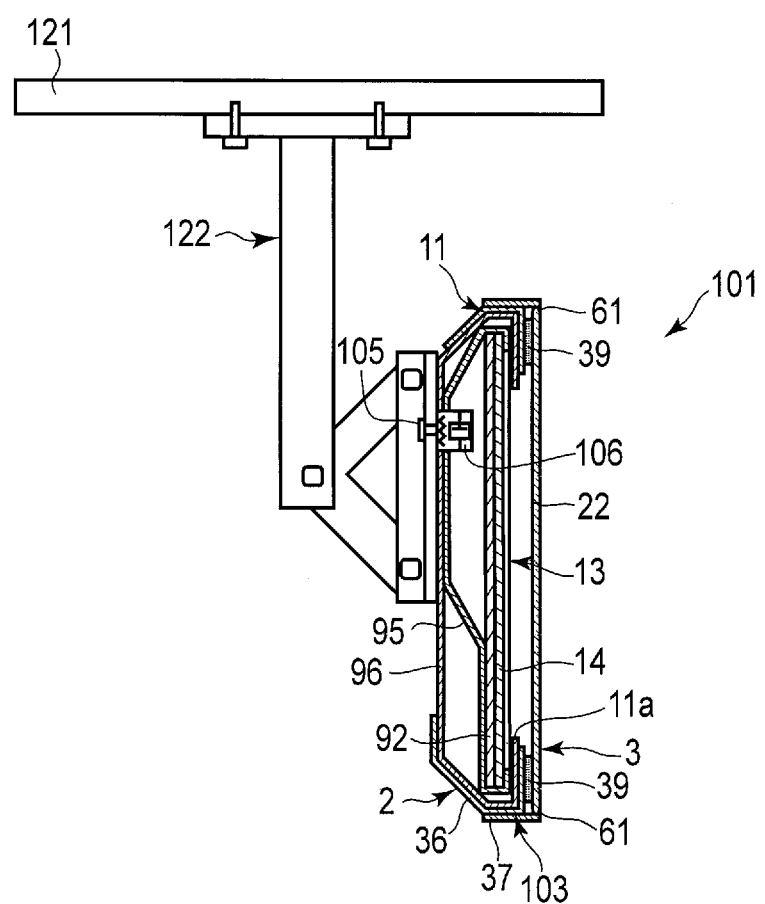
FIG. 23 is a cross-sectional view illustrating the video display unit according to a fifth modification of the fifth embodiment.

FIG. 23 shows the video display unit 101 according to the fifth modification of the fifth embodiment. In the present modification, the shock absorber 106 is provided in the display unit 103 instead of being provided in the mounting member 122. The shock absorber 106 is provided between a member which is structurally independent of the display 13 and an installation unit (for example, the mounting member 122).

Specifically, in the present modification, the shock absorber 106 is provided at a portion to which the mounting member 122 of the display unit 103 is fixed. The shock absorber 106 is provided, for example, between the back wall 96 of the housing 11 and the mounting member 122.

The housing 11 and the display 13 are supported by the mounting member 122 through the shock absorber 106, and are not directly fixed to the mounting member 122. Thus, part of shock and oscillation transmitted from the ceiling 121 to the mounting member 122 is absorbed by the shock absorber 106 before being transmitted to the protective cover 3. Large shock and oscillation are thereby hardly transmitted to the protective cover 3.

It should be noted that the present modification can be each applied to the structure in which the display unit 103 is supported by the wall-hung fitting 104 or the stand 12. That is, also in this structure, the shock absorber 106 may be provided in the display unit 103 instead of being provided in the installation unit.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic apparatus comprising:
a housing;
a display panel accommodated in the housing, the display panel comprising a display screen;
a phototransmissive front panel comprising a first surface facing the display screen, a second surface being located on an opposite side to the first surface and exposed to an outside, and a locking surface being provided along at least one side of the second surface and located inward of the second surface in the housing in a thickness direction of the display panel; and
a support portion provided in the housing, the support portion facing the locking surface from the outside in the thickness direction of the display panel,
wherein the locking surface is a slope extending from an edge of the second surface, being inclined with respect to the second surface, and
the support portion comprises a slope extending substantially parallel to the locking surface.

2. The electronic apparatus of claim 1, wherein the support portion is provided outside a region facing the second surface in the thickness direction of the display panel.

3. The electronic apparatus of claim 1, wherein the housing comprises a front surface exposed forward of the electronic apparatus in the thickness direction of the display panel, and
the second surface of the front panel and the front surface of the housing are located on substantially the same plane.

4. The electronic apparatus of claim 1, wherein the front panel is formed in a rectangle, and comprises a first side and a second side facing each other,
the locking surface is provided along each of the first side and the second side, and
the housing comprises the support portion at each portion adjacent to the first side and the second side.

5. The electronic apparatus of claim 4, wherein the front panel comprises a third side and a fourth side extending between the first side and the second side,
the housing comprises an opening through which the second surface of the front panel is exposed, and
gaps are provided between an inner edge of the opening and the third side of the front panel and between the inner edge of the opening and the fourth side of the front panel.

6. The electronic apparatus of claim 5, wherein the front panel comprises a slope having substantially the same width as the locking surface on each of the third side and the fourth side, and
a width of the locking surface exposed through the opening is less than a width of the slope of the third side exposed through the opening.

7. The electronic apparatus of claim 6, further comprising an infilling member inserted in each of the gap between the inner edge of the opening and the third side of the front panel and the gap between the inner edge of the opening and the fourth side of the front panel.

8. The electronic apparatus of claim 7, wherein the infilling member comprises a projection facing the slope of the third side from the outside in the thickness direction of the display panel.

9. The electronic apparatus of claim 4, wherein the front panel is formed in a rectangle,
the locking surface is provided along each of the four sides of the front panel, and
the housing comprises the support portion at each portion adjacent to the four sides of the front panel.

10. A video display unit comprising:
a video display apparatus; and
a cover mounted on the video display apparatus,
wherein the video display apparatus comprising:
a housing provided with an opening, and
a display panel accommodated in the housing, the display panel being exposed through the opening; and
the cover comprising:
a frame mounted on the housing of the video display apparatus,
a phototransmissive front panel held by the frame, the phototransmissive front panel comprising a first surface facing the display panel, a second surface being located on an opposite side to the first surface and exposed to an outside, and a locking surface being provided along at least one side of the second surface and located inward of the second surface in the frame in a thickness direction of the display panel, and a support portion provided in the frame, the support portion facing the locking surface from the outside in the thickness direction of the display panel, wherein the locking surface is a slope extending from an edge of the second surface, being inclined with respect to the second surface, and the support portion includes a slope extending substantially parallel to the locking surface.

11. The video display unit of claim 10, wherein the frame comprises a front surface exposed forward of the cover in the thickness direction of the display panel, and the second surface of the front panel and the front surface of the frame are located on substantially the same plane.

12. The video display unit of claim 10, wherein the front panel is formed in a rectangle and comprises a first side and a second side facing each other, the locking surface is provided along each of the first side and the second side, and the frame comprises the support portion at each portion adjacent to the first side and the second side.

* * * * *